US012678184B2

(12) United States Patent　　　(10) Patent No.:　US 12,678,184 B2

Shelton, IV et al.　　　(45) Date of Patent:　　Jul. 14, 2026

(54) AUTONOMOUS INTRA-INSTRUMENT SURGICAL SYSTEM ACTUATION

(71) Applicant: Cilag GmbH International, Zug (CH)

(72) Inventors: Frederick E. Shelton, IV, Hillsboro, OH (US); Charles J. Scheib, Loveland, OH (US); Kevin M. Fiebig, Cincinnati, OH (US); Taylor W. Aronhalt, Loveland, OH (US)

(73) Assignee: Cilag GmbH International, Zug (CH)

( * ) Notice: Subject to any disclaimer, the term of this patent is extended or adjusted under 35 U.S.C. 154(b) by 807 days.

(21) Appl. No.: 17/747,777

(22) Filed: May 18, 2022

(65) Prior Publication Data

US 2023/0371968 A1　　　Nov. 23, 2023

(51) Int. Cl.
　　　*A61B 18/12*　　　(2006.01)
　　　*A61B 17/285*　　　(2006.01)
　　　　　(Continued)

(52) U.S. Cl.
　　　CPC ........... *A61B 17/285* (2013.01); *G16H 40/67* (2018.01); *A61B 2017/00022* (2013.01); *A61B 2017/00141* (2013.01)

(58) Field of Classification Search
　　　CPC ... A61B 18/1445; A61B 18/085; A61B 18/12; A61B 18/1206; A61B 18/1442; A61B 2018/1452; A61B 2018/1455; A61B 2018/00607; A61B 2018/00589; A61B 2018/00595; A61B 2018/00601; A61B 2018/00619; A61B 2018/0063;
　　　　　(Continued)

(56) References Cited

U.S. PATENT DOCUMENTS 9,345,481 B2　　5/2016　Hall et al.
9,820,823 B2 *　11/2017　Richmond ............. A61B 34/74
　　　　　(Continued)

FOREIGN PATENT DOCUMENTS

EP　　1854420 A1　　11/2007
EP　　3231373 A2　　10/2017
　　　　(Continued)

OTHER PUBLICATIONS

Kazanzides, P et al., "Force sensing and control for a surgical robot", Proceedings of the International Conference on Robotics and Automation Nice, France, May 12-14, 1992, pp. 612-617.

*Primary Examiner* — Thomas A Giuliani

(74) *Attorney, Agent, or Firm* — Condo Roccia Koptiw LLP

(57)　　　　ABSTRACT

Systems, methods, and instrumentalities are described herein for autonomous operation of a surgical device within a predefined boundary. A discrete signal associated with clamping control (e.g., closure of a clamping jaw) may be received by the surgical device. The discrete signal may be triggered by a healthcare professional or autonomously activated. The surgical device, in response to the discrete signal and based on an algorithm, may generate a continuous signal to cause a continuous application of force or deployment of an operation. The surgical device, based at least on a measurement associated with one of tissue, inrush current, or the distance between the smart energy device and the smart grasper may determine a safety adjustment associated with the operation of the surgical device.

20 Claims, 15 Drawing Sheets

(51) Int. Cl.
   *G16H 40/67*        (2018.01)
   *A61B 17/00*        (2006.01)
(58) Field of Classification Search
   CPC ........... A61B 2018/00642; A61B 2018/00702;
            A61B 2018/126; A61B 17/285; A61B
            17/320092; A61B 2017/00022; A61B
                                      2017/00017
   USPC ............... 606/34, 37, 38, 41, 42, 45, 48–52;
                       607/98, 99, 101, 115, 116
   See application file for complete search history.

(56)                References Cited

U.S. PATENT DOCUMENTS

| | | | | |
|---|---|---|---|---|
| 10,314,644 | B2 * | 6/2019 | Brogna | A61B 18/1445 |
| 10,881,399 | B2 | 1/2021 | Shelton, IV et al. | |
| 11,589,888 | B2 | 2/2023 | Shelton, IV et al. | |
| 11,617,492 | B2 | 4/2023 | Refai et al. | |
| 2011/0015632 | A1 * | 1/2011 | Artale | A61B 18/1445 |
| | | | | 606/51 |
| 2012/0116391 | A1 * | 5/2012 | Houser | A61B 34/76 |
| | | | | 606/1 |
| 2014/0263552 | A1 | 9/2014 | Hall et al. | |
| 2015/0088122 | A1 * | 3/2015 | Jensen | A61B 18/1445 |
| | | | | 606/37 |
| 2016/0030134 | A1 | 2/2016 | Shapter et al. | |
| 2017/0172594 | A1 * | 6/2017 | Allen, IV | A61B 18/1445 |
| 2017/0189102 | A1 * | 7/2017 | Hibner | A61B 90/98 |
| 2017/0296213 | A1 | 10/2017 | Swensgard et al. | |
| 2019/0200844 | A1 | 7/2019 | Shelton, IV et al. | |
| 2019/0200977 | A1 | 7/2019 | Shelton, IV et al. | |
| 2019/0200981 | A1 | 7/2019 | Harris et al. | |
| 2019/0201046 | A1 * | 7/2019 | Shelton, IV | G16H 50/20 |
| 2019/0201047 | A1 | 7/2019 | Yates et al. | |
| 2019/0201137 | A1 | 7/2019 | Shelton, IV et al. | |
| 2019/0201140 | A1 | 7/2019 | Yates et al. | |
| 2019/0206542 | A1 | 7/2019 | Shelton, IV et al. | |
| 2019/0206562 | A1 | 7/2019 | Shelton, IV et al. | |
| 2019/0206569 | A1 | 7/2019 | Shelton, IV et al. | |
| 2019/0231220 | A1 | 8/2019 | Refai et al. | |
| 2020/0405403 | A1 | 12/2020 | Shelton, IV et al. | |
| 2021/0205031 | A1 | 7/2021 | Shelton, IV et al. | |
| 2021/0298795 | A1 | 9/2021 | Bowling et al. | |
| 2021/0322017 | A1 | 10/2021 | Shelton, IV et al. | |
| 2021/0370790 | A1 | 12/2021 | Feldman | |
| 2022/0108789 | A1 | 4/2022 | Shelton, IV et al. | |
| 2022/0233119 | A1 | 7/2022 | Shelton, IV et al. | |
| 2022/0354347 | A1 | 11/2022 | Nishimura et al. | |
| 2023/0028059 | A1 | 1/2023 | Shelton, IV et al. | |
| 2023/0371950 | A1 | 11/2023 | Shelton, IV et al. | |
| 2023/0371968 | A1 | 11/2023 | Shelton, IV et al. | |
| 2023/0372012 | A1 | 11/2023 | Harris et al. | |
| 2023/0372013 | A1 | 11/2023 | Shelton, IV et al. | |
| 2023/0372030 | A1 | 11/2023 | Shelton, IV et al. | |
| 2023/0372031 | A1 | 11/2023 | Shelton, IV | |
| 2023/0377709 | A1 | 11/2023 | Shelton, IV et al. | |
| 2023/0377726 | A1 | 11/2023 | Shelton, IV et al. | |
| 2023/0397969 | A1 | 12/2023 | Shelton, IV et al. | |
| 2023/0404691 | A1 | 12/2023 | Shelton, IV et al. | |

FOREIGN PATENT DOCUMENTS

| | | |
|---|---|---|
| EP | 3506287 A1 | 7/2019 |
| WO | 2018142277 A1 | 8/2018 |
| WO | 2019117926 A1 | 6/2019 |
| WO | 2021049438 A1 | 3/2021 |

* cited by examiner

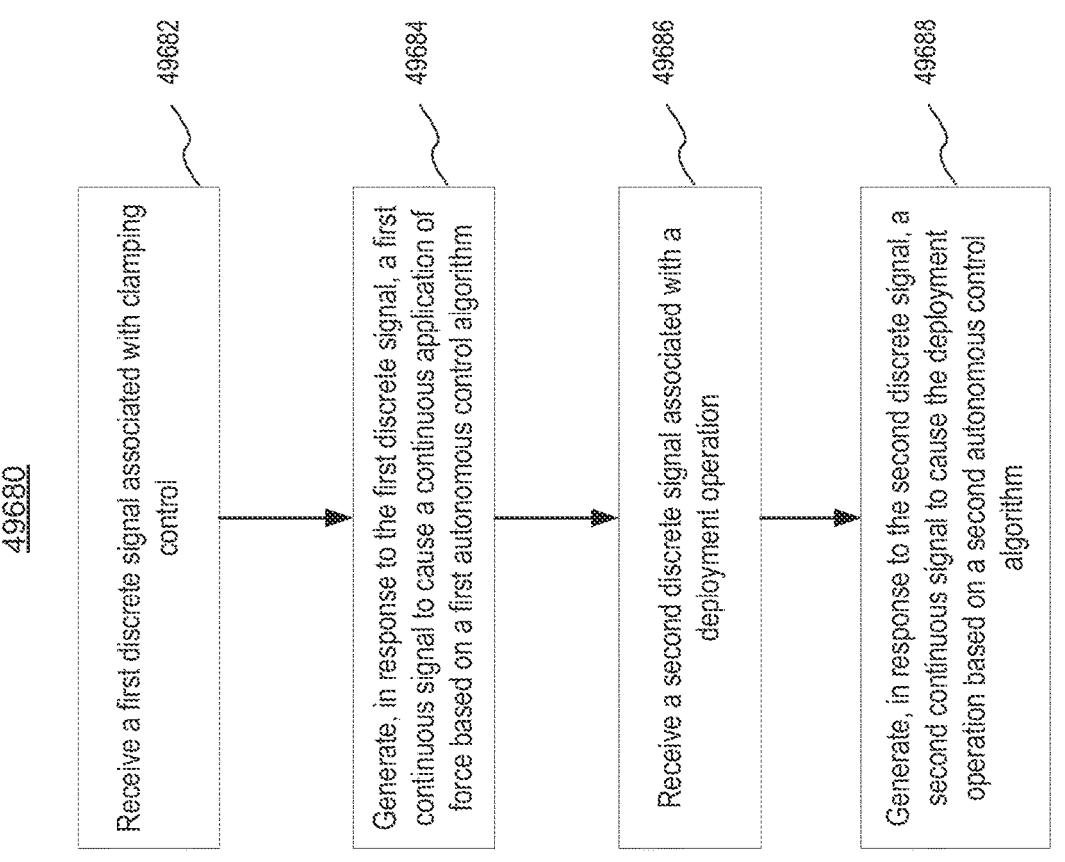

49680

Receive a first discrete signal associated with clamping control

49682

Generate, in response to the first discrete signal, a first continuous signal to cause a continuous application of force based on a first autonomous control algorithm

49684

Receive a second discrete signal associated with a deployment operation

49686

Generate, in response to the second discrete signal, a second continuous signal to cause the deployment operation based on a second autonomous control algorithm

Linear
Stapler

49840

Control a surgical device to operate autonomously within a predefined boundary — 49842

Based on a condition being satisfied, determine a safety adjustment to the operation — 49844

Control the surgical device to operate based on the safety adjustment — 49846

AUTONOMOUS INTRA-INSTRUMENT SURGICAL SYSTEM ACTUATION

CROSS-REFERENCE TO RELATED APPLICATIONS

This application is related to the following, filed contemporaneously, the contents of each of which are incorporated by reference herein:

U.S. patent application Ser. No. 17/747,806, entitled METHOD OF CONTROLLING AUTONOMOUS OPERATIONS IN A SURGICAL SYSTEM.

U.S. patent application Ser. No. 17/747,795, entitled AUTONOMOUS SURGICAL SYSTEM INSTRU-MENT ACTUATION.

BACKGROUND

Surgical procedures performed using surgical systems or surgical devices may rely on healthcare professionals to control every aspect of the surgical systems or surgical devices during a surgical procedure. Current surgical systems and/or surgical devices may not be adequate for performing surgical procedures autonomously/

SUMMARY

Systems, methods, and instrumentalities are described herein for autonomous operation of a surgical device. For example, the surgical device may be a surgical cutting device or a surgical energy device. A first discrete signal associated with clamping control may be received by the surgical device. The first discrete signal may be associated with initiating closure of a clamping jaw. The first discrete signal may be triggered by a healthcare professional or autonomously activated. The surgical device, in response to the first discrete signal, may generate a first continuous signal to cause a continuous application of force based on a first autonomous control algorithm. For example, the continuous application of force may be adjusted autonomously based on at least a first measurement (e.g., a measurement associated with a tissue).

A second discrete signal associated with clamping control may be received by the surgical device. The second discrete signal may be associated with initiating a firing sequence. The second discrete signal may be triggered by a healthcare professional or autonomously activated. The deployment operation may be advancing of a cutting member and retracting of the cutting member. The surgical device, in response to the second discrete signal, may generate a second continuous signal to cause the deployment operation based on a second autonomous control algorithm. The second measurement may be a ratio of collagen to elastin in the tissue. The deployment operation may be adjusted autonomously based on at least the second measurement.

Systems, methods, and instrumentalities are described herein for autonomous operation of a surgical device within a predefined boundary. For example, the surgical device may be a smart grasper, a smart surgical stapler, or a smart energy device. The predefined boundary may be a virtual movement boundary associated with a surgical task. The predefined boundary may be a field of view defined by a scope device.

The surgical device, for example, a smart gasper, based at least on a condition that a tissue tension measurement associated with the smart grasper being equal to or greater than a maximum tissue tension may determine a safety adjustment to the operation of the smart grasper. The safety adjustment may be a reduction of grasping force. The surgical device, for example, a smart stapler, based at least on a condition that an inrush current measurement being below a lowest threshold may determine a safety adjustment to the operation of the smart stapler. The safety adjustment may be stopping a firing sequence. The surgical device, for example, a smart energy device, based at least on a condition that a distance between the smart energy device and the smart grasper is below a threshold may determine a safety adjustment to movement of the smart energy device based on one or more location data and orientation data.

BRIEF DESCRIPTION OF THE DRAWINGS

FIG. 10 is a flow chart of an example autonomous operation of a surgical instrument.

DETAILED DESCRIPTION

Figure 1:
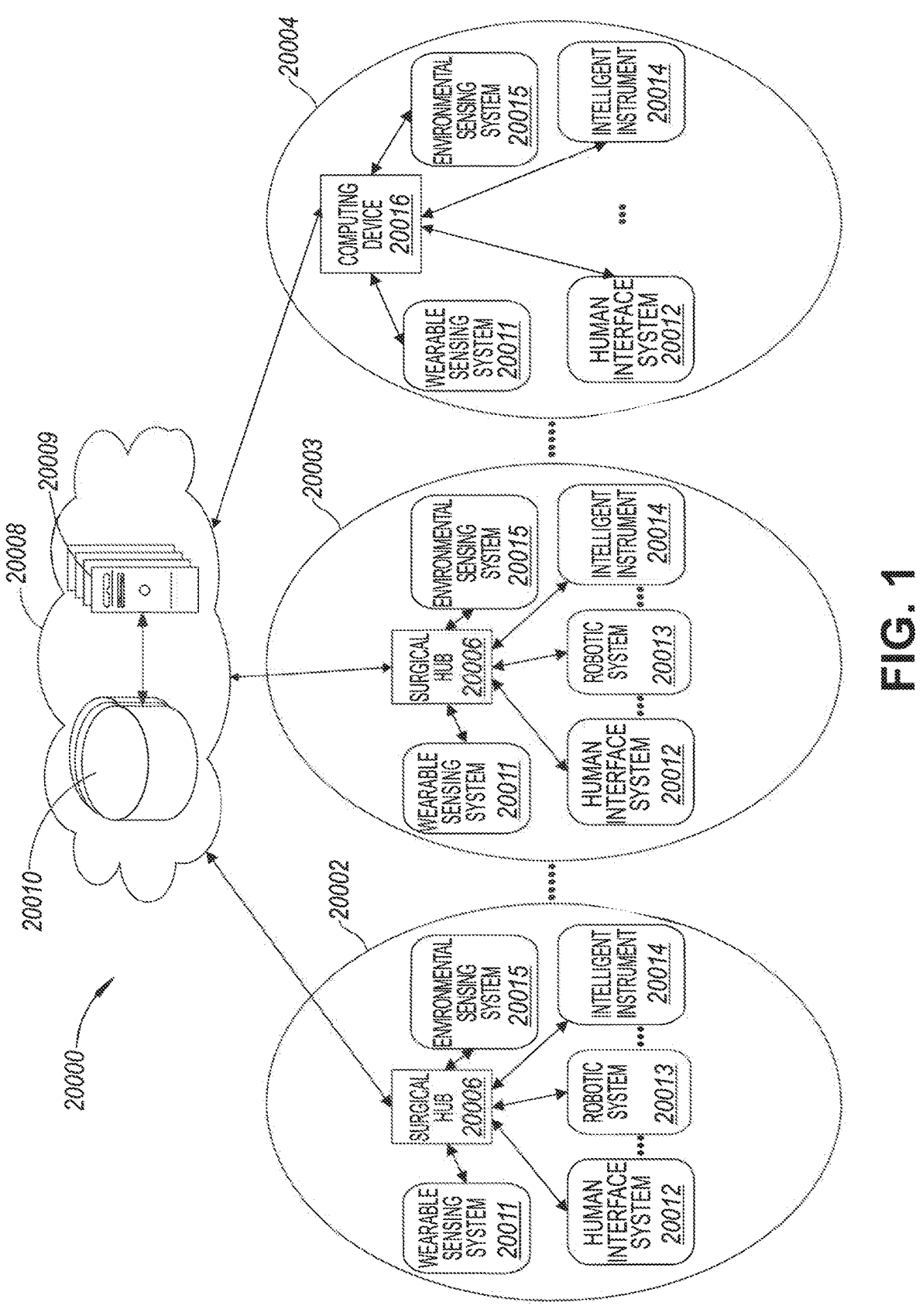
FIG. 1 is a block diagram of a computer-implemented surgical system.

FIG. 1 is a block diagram of a computer implemented surgical system 20000. An example surgical system such as the surgical system 20000 may include one or more surgical systems (e.g., surgical sub-systems) 20002, 20003 and 20004. For example, surgical system 20002 may include a computer-implemented interactive surgical system. For example, surgical system 20002 may include a surgical hub 20006 and/or a computing device 20016 in communication with a cloud computing system 2.0008, for example, as described in FIG. 2. The cloud computing system 20008 may include at least one remote cloud server 20009 and at least one remote cloud storage unit 20010. Example surgical systems 20002, 20003, or 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more HCP sensing systems, and/or one or more patient sensing systems. The environmental sensing system 20015 may include one or more devices, for example, used for measuring one or more environmental attributes, for example, as further described in FIG. 2. The robotic system 20013 may include a plurality of devices used for performing a surgical procedure, for example, as further described in FIG. 2.

The surgical system 20002 may be in communication with a remote server 20009 that may be part of a cloud computing system 20008. In an example, the surgical system 20002, may be in communication with a remote server 20009 via an internet service provider's cable/FIOS networking node. In an example, a patient sensing system may be in direct communication with a remote server 20009. The surgical system 20002 and/or a component therein may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

For example, the sensing systems 20001 may include the wearable sensing system 20011 (which may include one or more HCP sensing systems and one or more patient sensing systems) and the environmental sensing system 20015 as discussed in FIG. 1. The one or more sensing systems 20001, may measure data relating to various biomarkers. The one or more sensing systems 20001 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are nor limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 20000, for example. The information from the biomarkers may be determined and/or used by the computer-implemented patient and the surgical system 20000 to improve said systems and/or to improve patient outcomes, for example. The one or more sensing systems 20001, biomarkers 20005, and physiological systems are described in more detail in U.S. application Ser. No. 17/156,287, titled METHOD OF ADJUSTING A SURGICAL PARAMETER BASED ON BIOMARKER. MEASUREMENTS, filed Jan. 22, 2021, the disclosure of which is herein incorporated by reference in its entirety.

Figure 2:
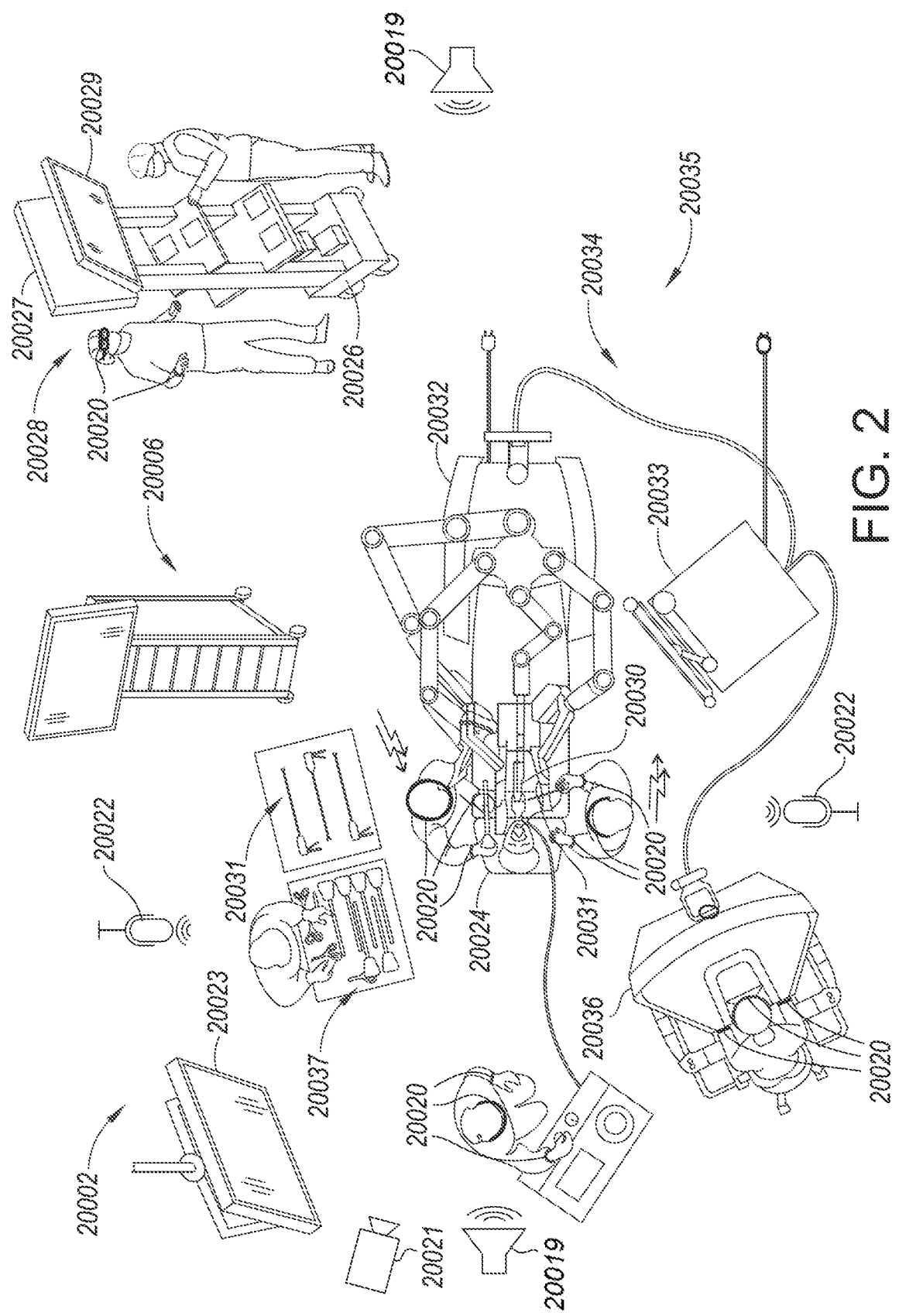
FIG. 2 shows an example surgical system in a surgical operating room.

FIG. 2 shows an example of a surgical system 20002 in a surgical operating room. As illustrated in FIG. 2, a patient is being operated on by one or more health care professionals (HCPs). The HCPs are being monitored by one or more HCP sensing systems 20020 worn by the HCPs. The HCPs and the environment surrounding the HCPs may also be monitored by one or more environmental sensing systems including, for example, a set of cameras 20021, a set of microphones 20022, and other sensors that may be deployed in the operating room. The HCP sensing systems 20020 and the environmental sensing systems may be in communication with a surgical hub 20006, which in turn may be in communication with one or more cloud servers 20009 of the cloud computing system 20008, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary RID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2, a surgical instrument 20031 is being used in the surgical procedure as part of the surgical system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, ate described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and e or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that conies in contact with the patient or penetrates tile sterile field, including the imaging device 20030 and its attachments and components. It will be appreciated that the sterile field may be considered a specified area, such as within a tray or on a sterile towel, that is considered free of microorganisms, or tile sterile field may be considered an area, immediately around a patient, who has been prepared for a surgical procedure. The sterile field may include the scrubbed team members, who are properly attired, and all furniture and fixtures in the area, Wearable sensing system 20011 illustrated in FIG. 1 may include one or more sensing systems, for example, HCP sensing systems 20020 as shown in FIG. 2. The HCP sensing systems 20020 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 20020 may measure a set of biomarkers to monitor the heart rate of an HCP. In an example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include micro-phones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 20020 may measure one or more surgeon biomarkers associated with an HCP and send the measurement data associated with the surgeon biomarkers to the surgical hub 20006. The HCP sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control pro-gram to a surgical instrument 20031 to control its actuators to limit or compensate for fatigue and use of fine motor skills. The surgical hub 20006 may send the control program based on situational awareness and/or the context on impor-tance or criticality of a task. The control program may instruct the instrument to alter operation to provide more control when control is needed.

Figure 3:
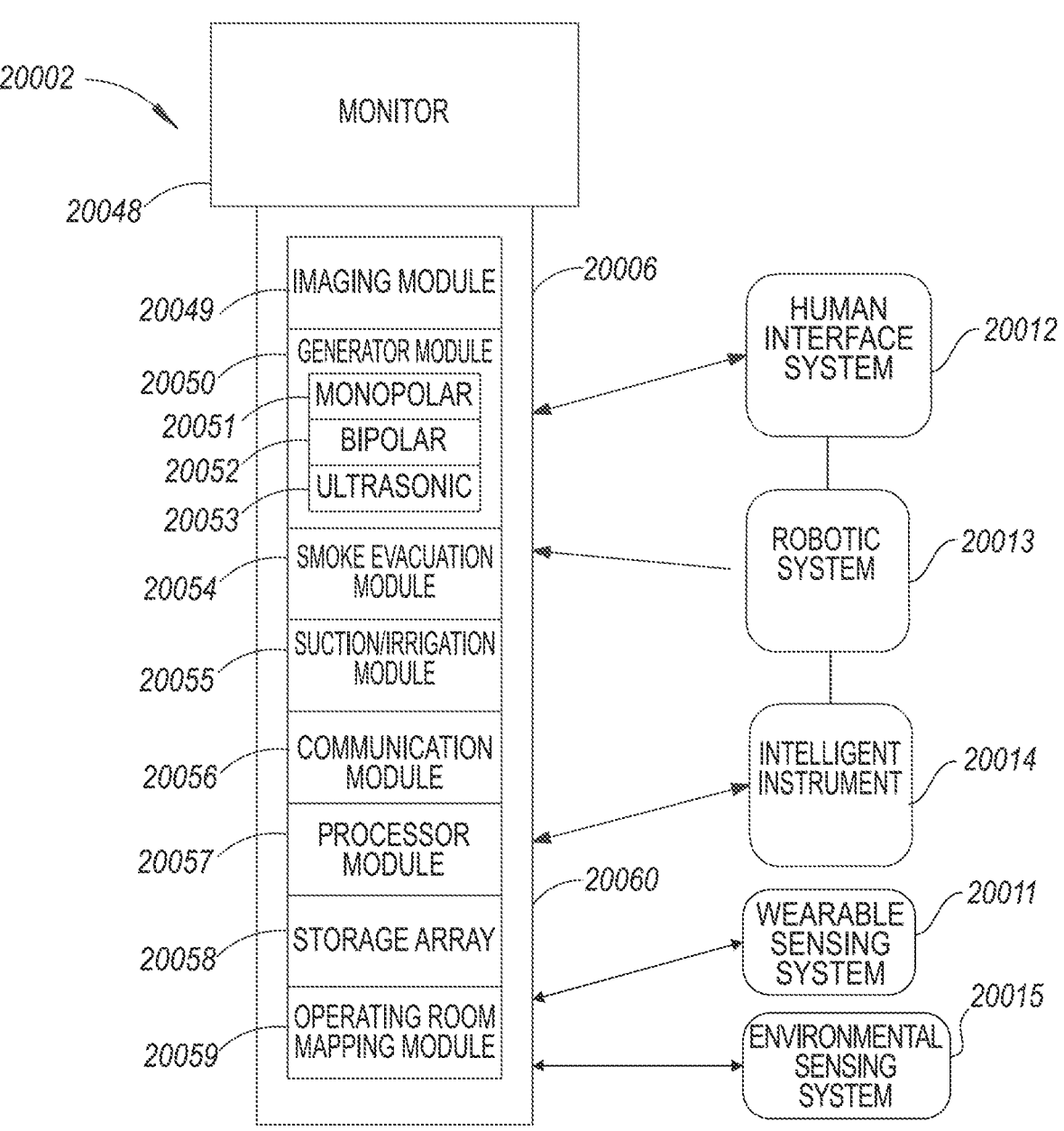
FIG. 3 illustrates an example surgical hub paired with various systems.

FIG. 3 shows an example surgical system 20002 with a surgical hub 20006. The surgical hub 20006 may be paired with, via a modular control, a wearable sensing system 20011, an environmental sensing system 20015, a human interface system 20012, a robotic system 20013, and an intelligent is 20014. The hub 20006 includes a display 20048, an imaging module 20049, a generator module 20050, a communication module 20056, a processor module 20057, a storage array 20058, and an operating-room map-ping module 20059. In certain aspects, as illustrated in FIG. 3, the hub 20006 further includes a smoke evacuation module 20054 and/or a suction/irrigation module 20055. The various modules and systems may be connected to the modular control either directly via a router or via the communication module 20056. The operating theater devices may be coupled to cloud computing resources and data storage via the modular control. The human interface system 20012 may include a display sub-system and a notification sub-system.

The modular control may be coupled to non-contact sensor module. The non-contact sensor module may mea-sure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmit-ting a burst of ultrasound and receiving the echo when it bounces off the perimeter walls of an operating theater as described under the heading "Surgical Hub Spatial Aware-ness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclo-sure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclo-sure 20060 and a combo generator module slidably receiv-able in a docking station of the hub enclosure 20060. The docking station includes data and power contacts. The combo generator module includes two or more of an ultra-sonic energy generator component, a bipolar RF energy generator component, and a monopolar RE energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a First energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present: disclosure are presented for a hub modular enclosure 20060 that allows the modular integration of a generator module 20050, a smoke evacuation module 20054, and a suction/irrigation module 20055. The huh modular enclosure 20060 further facilitates interactive communication between the modules 20059, 20054, and 20055. The generator module 20050 can be with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
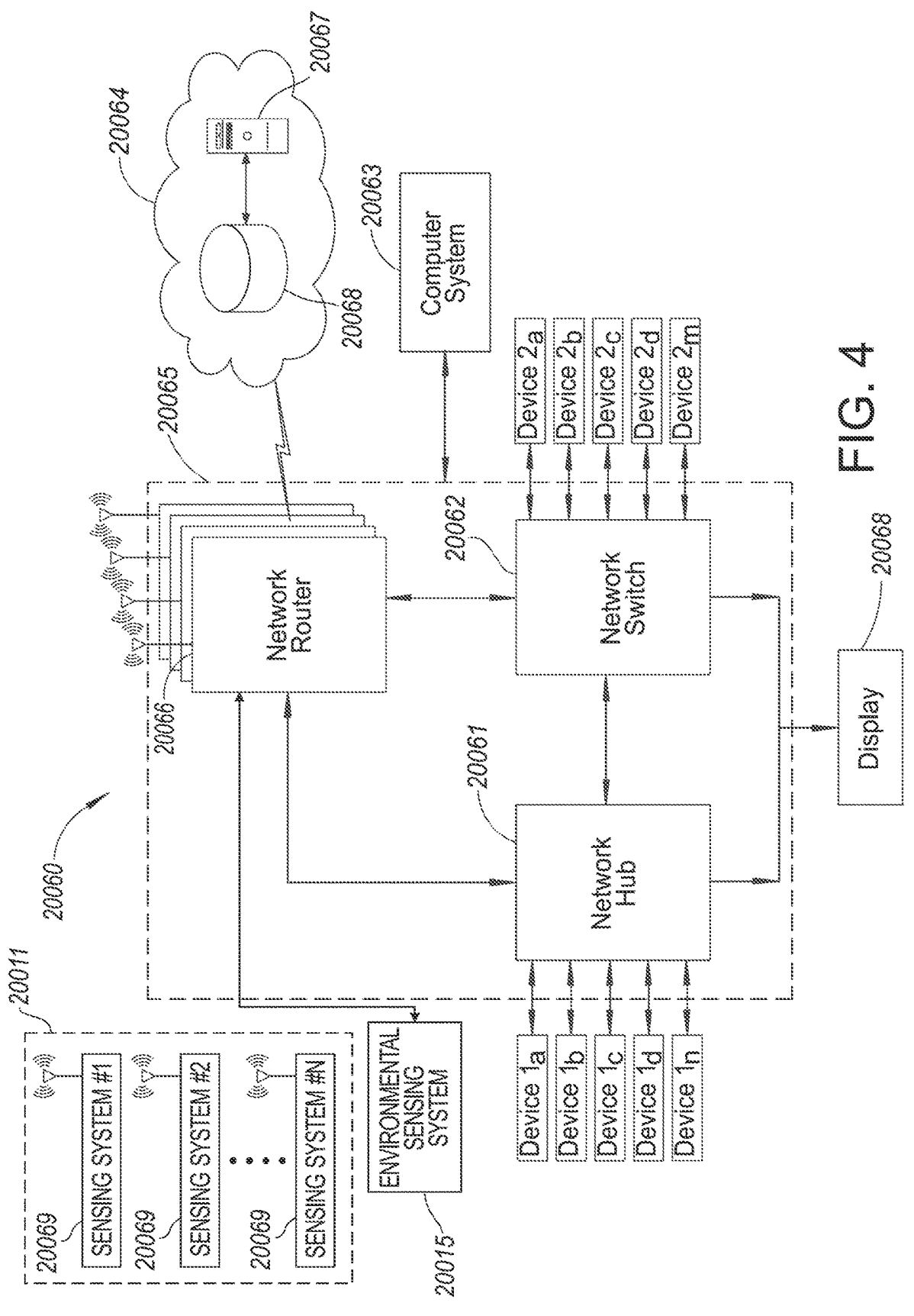
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs con figured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present: disclosure.

As illustrated in. FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a. local computer system 20063 to provide local computer processing and data manipulation.

The computer system 20063 may comprise a processor and a network interface 20100. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

in an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety- features while delivering scalable performance, connectivity, and memory options.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A User may enter commands or information into the computer system 20063 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use sonic of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like integrated Services Digital Networks (ISDN) and variations thereon, packet-switching networks, and Digital Subscriber Lines (DSl).

In various examples, the computer system 20063 may comprise an image processor, image-processing engine, media processor, or any specialized digital signal processor (DSP) used for the processing of digital images, The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1*a*-1*n* located in the operating theater may be coupled to the modular communication hub 20065. The network hub 20061 and/or the network switch 20062 may coupled to a network router 20066 to connect the devices 1*a*-1*n* to the cloud computing system 20064 or the local computer system 20063. Data associated with the devices 1*a*-1*n* may be transferred to cloud-based computers via the router for remote data processing and manipulation. Data associated with the devices 1*a*-1*n* may also be transferred to the local computer system 20063 for local data processing and manipulation. Modular devices 2*a*-2*m* located in the same operating theater also may be coupled to a network switch 20062. The network switch 20062 may be coupled to the network hub 20061 and/or the network router 20066 to connect the devices 2*a*-2*m* to the cloud 20064. Data associated with the devices 2*a*-2*m* may be transferred to the cloud computing system 20064 via the network router 20066 for data processing and manipulation. Data associated with the devices 2*a*-2*m* may also be transferred to the local computer system 20063 for local data processing and Manipulation.

The wearable sensing system 20011 may include one or more sensing systems 20069. The sensing systems 20069 may include an HCP sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endo- scope, a generator module coupled to an energy-based surgical device, a smoke evacuation module, a suction/ irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1a-1n/2a-2m of the sensing systems 20069 to the cloud-base system 20064. One or more of the devices 1a-1n/2a-2m or the sensing systems 20069 coupled to the network hub 20061 or network switch 20062 may collect data in real-time and transfer the data to cloud computers for data processing, and manipulation. It will be appreciated that cloud computing relies on sharing computing resources rather than having local servers or personal devices to handle software applications. The word "cloud" may be used as a metaphor for "the Internet," although the term is not limited as sects. Accordingly, the term "cloud computing" may be used herein to refer to "a type of Internet-based computing," where different services—such as servers, stor- age, and applications—are delivered to the modular com- munication hub 20065 and/or computer system 20063 located in the surgical theater (e.g., a fixed, mobile, tempo- rary, or field operating room or space) and to devices connected to the modular communication hub 20065 and/or computer system 20063 through the Internet. The cloud infrastructure may be maintained by a cloud service pro- vider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, sensing systems, and other computer- ized devices located in the operating theater. The hub hardware enables multiple devices, sensing systems, and/or connections to be connected to a computer that communi- cates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathol- ogy, such as the effects of diseases, using the cloud-based computing to examine data including images of samples of body tissue for diagnostic purposes. This may include local- ization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud computing system 20064 or the local computer system 20063 or both for data processing and manipulation including image pro- cessing and manipulation. The data may be analyzed to improve surgical procedure outcomes by determining if farther treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 2006 the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recov- ering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, and notify a patient of a complication during post-surgical period.

The operating theater devices 1a-1n may be connected to the modular communication hub 20065 over a wired channel or a wireless channel depending on the configuration of the devices 1a-1n to a network hub 20061. The network hub 20061 may be implemented, in one aspect, as a local network broadcast device that works on the physical layer of tile Open System Interconnection (OSI) model. The network hub may provide connectivity to the devices 1a-1n located in the same operating theater network. The network hub 20061 may collect data in the form of packets and sends them to the router in half duple mode. The network hub 200611 may not store any media access control/Internet Protocol (MAC/IP) to transfer the device data. Only one of the devices 1a-1n can send data at a time through the network hub 20061. The network hub 20061 may not have routing tables or intelligence regarding where to send infor- mation and broadcasts all network data across each connec- tion and to a remote server 20067 of the cloud computing system 20064. The network hub 20061 can detect basic network errors such as collisions but having all information broadcast to multiple ports can be a security risk and cause bottlenecks.

The operating theater devices 2a-2m may be connected to a network switch 20062 over a wired channel or a wireless channel. The network switch 20062 works in the data link layer of the OSI model. The network switch 20062 may be a multicast device for connecting the devices 2a-2m located in the same operating theater to the network. The network switch 20062 may send data in the form of frames to the network router 20066 and may work in full duplex mode. Multiple devices 2a-2m can send data at the same time through the network switch 20062. The network switch 20062 stores and uses MAC addresses of the devices 2a-2m to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for farther processing and manipulation of the data collected by any one of or all the devices 1a-1n/2a-2m and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20064 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m and/or the sensing systems 20069 may communicate to the modular communication hub 20065 via. Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1a-1n/2a-2m and the sensing systems 20069 and may handle a data type known as frames. Frames may carry the data generated by the devices 1a-1n/2a-2m and/or the sensing systems 20069. When a frame is received by the modular communication hub 20065, it may be amplified and sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1a-1n/2a-2m.

Figure 5:
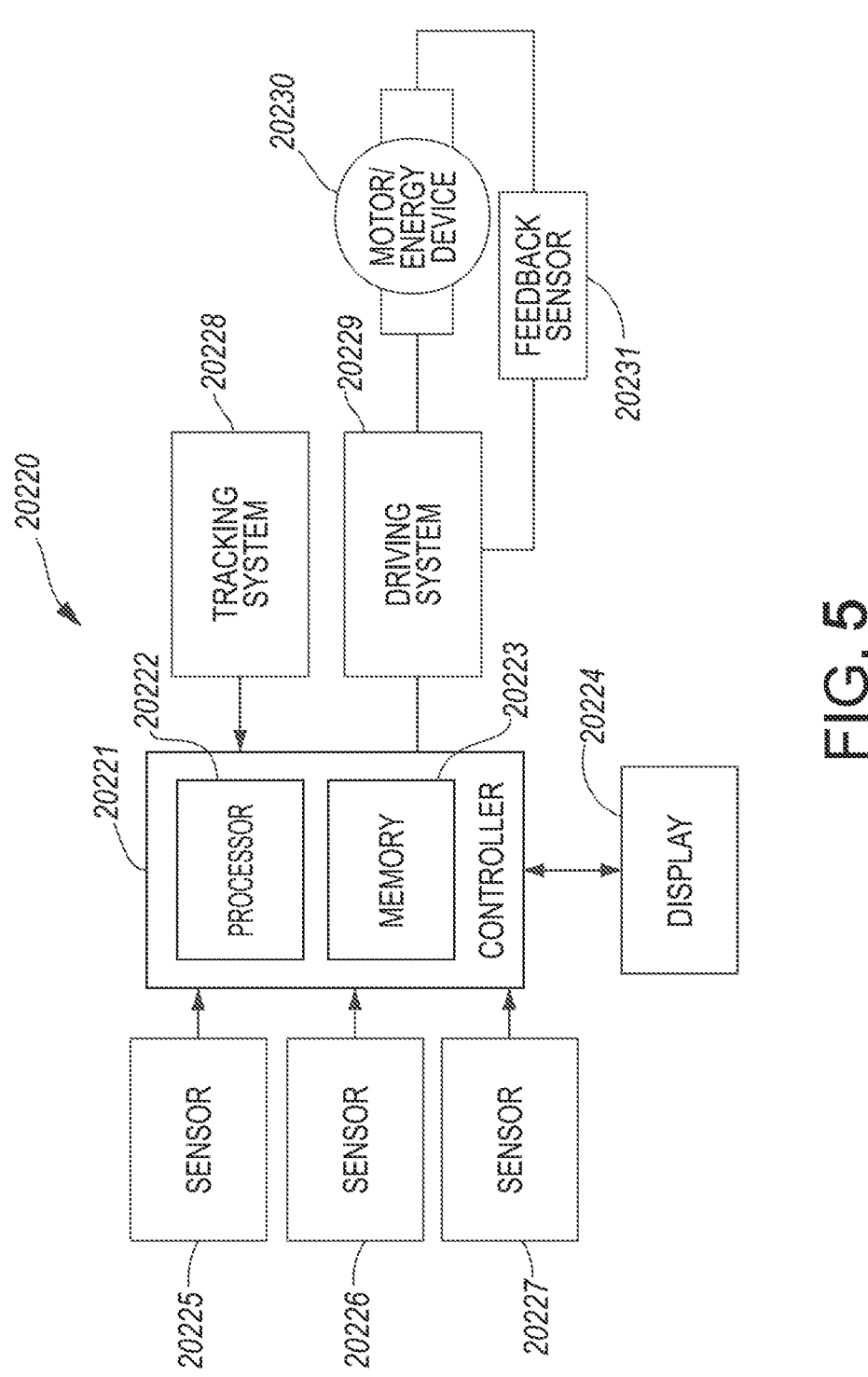
FIG. 5 illustrates a logic diagram of a control system of a surgical instrument.

FIG. 5 illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

The microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding, to the longitudinal linear displacement $d1+d2+ . . . dn$ of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiberoptic, magneto-optic, and microelectromechanical systems-based magnetic sensors, among others.

The position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning: system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 20117, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, Cr example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

For example, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the surgical hub 20065 as shown in FIG. 4.

Figure 6:
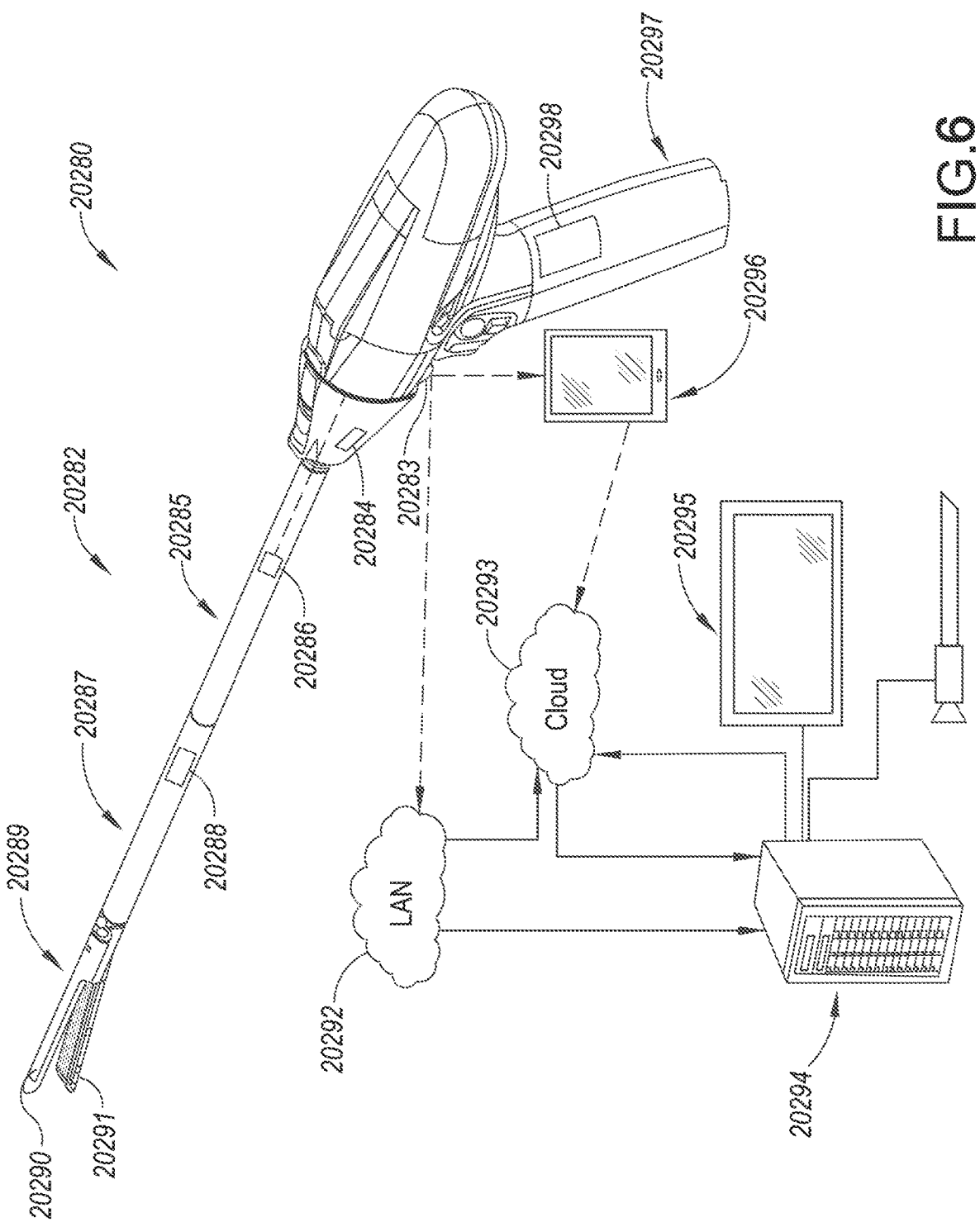
FIG. 6 shows an example surgical system that includes a handle having a controller and a motor, an adapter releasably coupled to the handle, and a loading unit releasably coupled to the adapter.

FIG. 6 illustrates an example surgical system 20280 in accordance with the present disclosure and may include a surgical instrument 20282 that can be in communication with a console 20294 or a portable device 20296 through a local area network 20292 and/or a cloud network 20293 via a wired and/or wireless connection. The console 20294 and the portable device 20296 may be any suitable computing device. The surgical instrument 20282 may include a handle 202.97, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touch screens, and any other suitable input mechanisms or user interfaces, which can be engaged by a clinician to activate the motor, The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 202.85 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of, the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit is data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub. The transceiver 20283 may receive data (e.g., cartridge data, loading unit data, adapter data, or other notifications) from the surgical hula 20270. The transceiver 20283 may receive data (e.g., cartridge data, loading unit data, or adapter it from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit: data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 7:
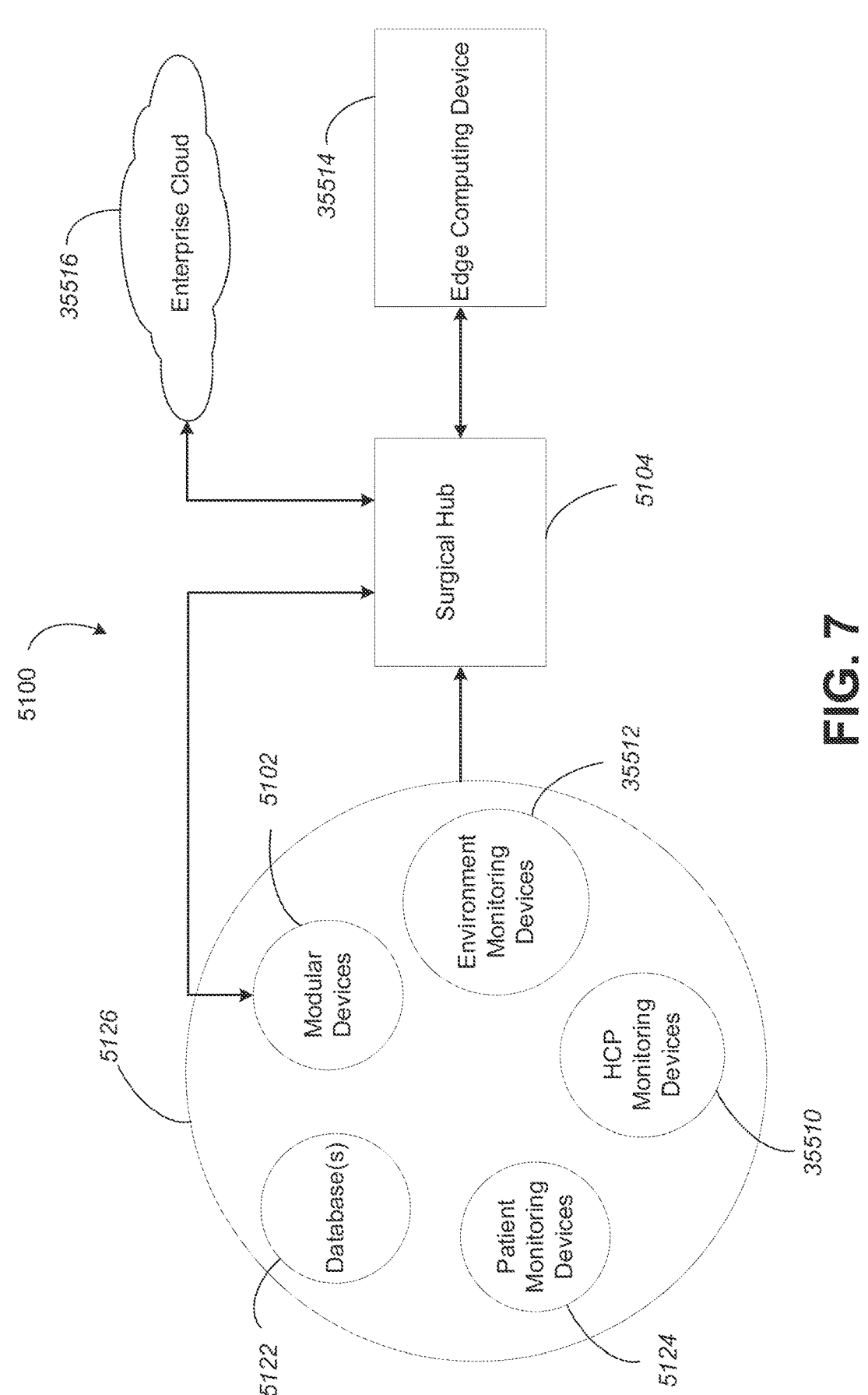
FIG. 7 shows an example situationally aware surgical system.

FIG. 7 illustrates a diagram of a situationally aware surgical system 5100, in accordance with at least one aspect of the present disclosure. The data sources 5126 may include, for example, the modular devices 5102 (which can include sensors configured to detect parameters associated with the patient, HCPs and environment and/or the modular device itself), databases 51122 (e.g., an EMR database containing patient records), patient monitoring devices 5124 (e.g., a blood pressure (BP) monitor and an electrocardiography (EKG) monitor), HCP monitoring devices 35510, and environment monitoring devices 35512. The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." For example, the surgical hub 5104 can incorporate a situational awareness system, which is the hardware and/or programming associated with the surgical hub 5104 that derives contextual information pertaining to the surgical procedure from the received data and/or a surgical plan information received from the edge computing system 35514 or an enterprise cloud server 35516.

The situational awareness system of the surgical hub 5104 can be configured to derive the contextual information from the data received from the data sources 5126 in a variety of different ways. For example, the situational awareness system can include a pattern recognition system, or machine learning system (e.g., an artificial neural network), that has been trained on training data to correlate various inputs (e.g., data from database(s) 5122, patient monitoring devices 5124, modular devices 5102, HCP monitoring devices 35510, and/or environment monitoring devices 35512) to corresponding contextual in formation regarding a surgical procedure. A machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual is formation received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RE power level or the ultrasonic amplitude of the generator (e.g., "energy level") to compensate for the fluid filled environment. belatedly, the type of tissue being operated on can affect the optimal energy level for an ultrasonic surgical instrument or RE electrosurgical instrument to operate at. A situationally aware surgical hub 5104 could determine what type of surgical procedure is being performed and then customize the energy level for the ultrasonic surgical instrument or RE electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (e.g., whether bleeding at a surgical site has stopped) according to video or image data received from a medical imaging device. The surgical hub 5104 can be further configured to compare a physiologic measurement (e.g., blood pressure sensed by a BP monitor communicably connected to the surgical hub 5104) with the visual or image data of hemostasis (e.g., from a medical imaging device communicably coupled to the surgical hub 5104) to make a determination on the integrity of the staple line or tissue weld. The situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use as soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could proactively change the displayed view (supplied by, e.g., a medical imaging device for the visualization system) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can compare the list of items for the procedure and/or a list of devices paired with the surgical hub 5104 to a recommended or anticipated manifest of items and devices for the given surgical procedure. If there are any discontinuities between the lists, the surgical hub 5104 can provide an alert indicating that a particular modular device 5102, patient monitoring device 5124, HCP monitoring devices 35510, environment monitoring devices 35512, and/or other surgical item is missing. In some examples, the surgical hub 5104 can determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other HCP(s)) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. The surgical hub 5104 can provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Figure 8:
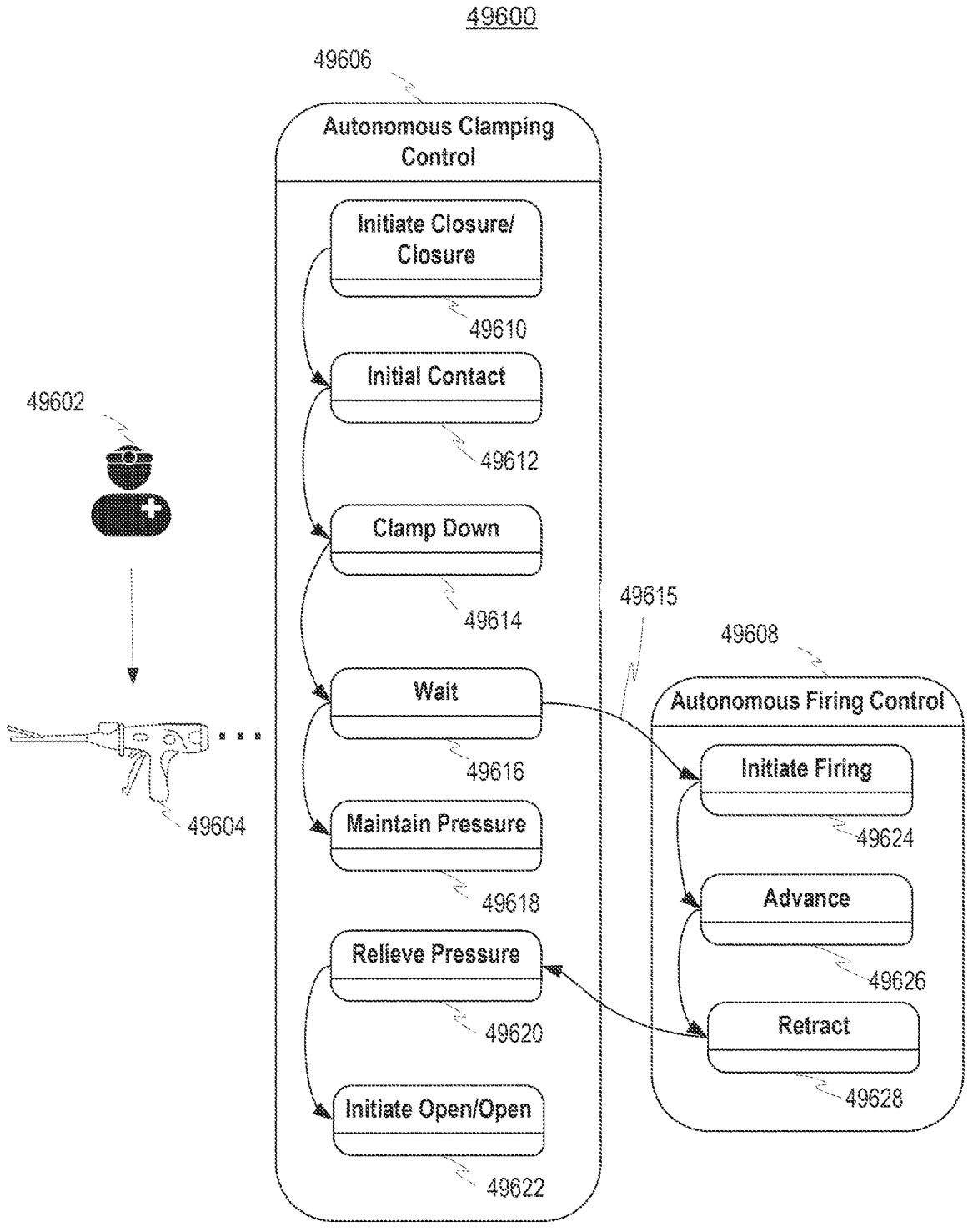
FIG. 8 illustrates an example autonomous operation of a surgical instrument.

FIG. 8 illustrates an example autonomous operation of a surgical instrument, 49600. The surgical instrument may be a smart surgical stapler. Additional details about operation of a smart stapler are disclosed in U.S. patent application Ser. No. 16/209,123, titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, the disclosure of which is herein incorporated by reference in its entirety.

A smart surgical stapler's operation may include clamping control and firing control. Clamping control may include control associated with one or more the following steps: initiating closure/closure of a clamping aw, initial contact with a tissue, clamping down (e.g., to a pre-determined pressure), wait (e.g., for a pre-determined period during which tissue creep occurs), maintaining pressure (e.g., during firing), relieving pressure (e.g., after firing is complete), initiate opening a clamping jaw/opening a clamping jaw. Firing control may include control associated with one or more the following steps: initiating firing (e.g., after wait), advancing a cutting member (e.g., a knife), firing staples, or retract the cutting member.

The smart surgical stapler's operation may include closure control. The closure control may include control associated with closing the clamping jaw (e.g., until the clamping jaw makes the initial contact with the tissue). A smart surgical instrument's operation may include opening control. The opening control may include control associated with opening the clamping jaw, for example, after the cutting member is retracted to the starting position.

A smart surgical stapler's operation may be controlled autonomously. The autonomous operation may be at different levels. One level of autonomous operation may include autonomously performing clamping down a clamping jaw to a pre-determined level (e.g., a pre-determined pressure or a pre-determined closure rate (e.g., 50% vs. fully closed)), wait (e.g., for a pre-determined period), initiating firing (e.g., after a pre-determined period of wait elapses), retracting a cutting member (e.g., after advancing of the cutting member is complete and staples are fired). One level of autonomous operation may include autonomously performing pre-defined clamping control between initial contact with a tissue and firing is ready to be initiated (e.g., when the wait period completes). One level of autonomous operation may include autonomously performing initiating firing and firing the cutting member to end-of-distal stroke and wait until manually indicated (e.g., by a surgeon) to retract the cutting member. One level of autonomous operation may include autonomously performing initiating firing, firing the cutting member to end-of-distal stroke, and retracting the cutting member to a starting position. One level of autonomous operation may include autonomously performing clamping down a clamping jaw to a pre-determined level, wait. initiating firing, retracting the cutting member, relieving pressure on the tissue (e.g., not including releasing the tissue /opening the clamping jaw).

The level of autonomous operation of a smart surgical stapler may be indicated by healthcare professional (e.g., a surgeon). A healthcare professional may actuate a clamping control trigger and at the end of the autonomous clamping control hold (e.g., keep pressed) the clamping control trigger. In such case, the clamping control operation may be autonomous, and the healthcare professional may take control back and perform manual firing control. A healthcare professional may actuate the clamping control trigger momentarily and may then release it In such case, the clamping control operation and the firing control operation may be autonomous. A healthcare professional may actuate the firing control trigger and then may hold the trigger. In such case, the firing control operation may be manual. A healthcare professional may actuate the firing control trigger and may then release it (e.g., after actuating the clamping control trigger first and then at the end of the autonomous clamping trigger hold the clamping control trigger, as described herein). In such case, the firing control operation may be autonomous (e.g., regardless of whether the clamping control operation is autonomous or manual). A healthcare professional may actuate and hold the clamping control trigger and then may actuate and hold the firing control trigger. In such case, the clamping control operation and the firing control operation may both be manual. healthcare professional may release a hold on an actuation control trigger (e.g., the clamping control trigger or the firing control trigger). In such case, the clamping control operation or the firing control operation may transition from manual to autonomous mode. A healthcare professional may reactivate a hold on an actuation control trigger (e.g., the clamping control trigger or the firing control trigger) when the clamping control operation or the firing control operation is during its autonomous operation. In such case, the clamping control operation or the firing control operation may transition from autonomous to manual. Further in such case, the healthcare professional may subsequently release the control trigger. In tins manner, the clamping control operation or the firing control operation may transition from manual to autonomous. A healthcare professional may actuate the opening control and release the control. In such case, the opening control operation may be autonomous. A healthcare professional may actuate the opening control and hold the control. In such case, the opening control operation may be manual.

As illustrated in FIG. 8, a smart surgical stapler 49604 may include a processor that is configured with one or more control algorithms for its autonomous operation. The smart surgical stapler 49604 may include a control system, for example, as described in FIG. 5. The smart surgical stapler 49604 may be configured with a control algorithm associated with autonomous clamping control operation 49606 ("autonomous clamping control algorithm"). The smart surgical stapler 49604 may be configured with a control algorithm associated with autonomous firing control operation 49608 ("autonomous firing control algorithm"). The smart surgical stapler 49604 may be configured with a control algorithm associated with the autonomous clamping control operation and the autonomous firing control operation. The autonomous clamping control algorithm 49606 may include one or more of the following: initiating closure 49610 of a clamping jaw, initial contact 49612 with a tissue, clamping down 49614 (e.g., to a pre-determined pressure), wait 49616 (e.g., before initiating firing 49624), maintaining pressure 49618 (e.g., during firing), relieving pressure 49620 (e.g., after firing is complete), or opening a clamping jaw 49622. The autonomous firing control algorithm 49608 may include one or more of the following: initiating firing 49624, advancing a cutting member 49626 (and associated staple firing), or retracting the cutting member 49628.

The smart surgical stapler 49604 may receive a first discrete signal associated with clamping control operation (e.g., via a control circuit). The first discrete signal may be initiated (e.g., via the control circuit) by healthcare professional's actuation of a clamping control trigger. In response to the first discrete signal, a first continuous signal may be generated (e.g., via the control circuit) to cause a continuous application of force (e.g., on a clamping jaw) based on autonomous clamping control algorithm 49606.

Based on autonomous clamping control algorithm 49606, the continuous application of force may cause a clamping jaw to clamp down 49614 to reach a predefined tissue compression pressure and/or to reach within a predefined range of tissue compression pressures (e.g., when fully closed). A clamping jaw may be caused to clamp down 49614 in a controlled manner. In an example, between the initial contact 496112 with the tissue and 50% closure of the clamping jaw, a first pre-defined rate of closure may be used. Between the 50% closure of the clamping jaw and when a predefined tissue compression pressure is reached, a second pre-defined rate of closure may be used. In an example, between the initial contact 49612 with the tissue and 50% closure of the clamping jaw, a first pre-defined rate of increase in tissue compression pressure may be used. Between the 50% closure of the clamping jaw and when a predefined tissue compression pressure is reached, a second pre-defined rate of increase in tissue compression pressure may be used.

Based on autonomous clamping control algorithm 49606, the first continuous signal may be adjusted autonomously. For example, the continuous signal may be adjusted based on one or more measurements. The continuous application of force may be adjusted to cause a clamping jaw to adjust its closure rate when clamping down 49614, e.g., based on a pre-defined tissue compression pressure limit (e.g., a tissue load limit). Tissue compression pressure limits (e.g., tissue load limits) may be based on safety characteristics, such as risk of tissue damage or other concerns such as excessive tissue movement. If the tissue compression pressure (e.g., sensed by the clamping jaw) is measurement to be about to exceed (e.g., have exceeded) a pre-defined tissue compression pressure limit, the closure rate may be reduced to a lower rate (e.g., a pre-defined lower rate) or the closure may be paused (e.g., paused completely). The closure may be paused for a pre-defined period, such as 1 or 2 seconds. Such reduction of closure rate or pause of closure may allow the tissue to viscoelastically relax. When the tissue compression pressure measurement falls under an acceptable threshold (e.g., a pre-defined threshold), the closure rate may be increased back to the previous closure rate or may be resumed to the previous closure rate, accordingly.

The continuous application of force may be adjusted to cause a clamping jaw to restrict clamping down 49614, e.g., based on tissue property measurement(s) (e.g., tissue impedance measurement(s), which may indicate presence of rigid object(s) if the measurements are higher than expected measurements associated with a tissue. Visual detection of rigid object(s) may be used to supplement tissue property measurements to detect presence of the rigid object(s). In response to detection of rigid object(s), the continuous application of force may pause to cause the clamping jaw to stop during clamping down 49614. In such case, a healthcare professional 49602 may be provided with an opportunity to address the detection (e.g., opening the clamping jaw and removing the detected rigid object(s) manually).

After the pre-defined tissue compression pressure is reached for a fully closed clamping jaw (e.g., after clamping down 49614 completes), the continuous application of force may cause the clamping jaw to hold the tissue for a pre-defined period of time (also known as wait time 49616/tissue creep) before firing(s) is/are initiated 49624 (e.g., based on autonomous firing control algorithm 49608, as described herein).

The continuous application of force may cause the clamping jaw to maintain pressure/grip 49618 on the tissue during the firing sequence (e.g., when firing(s) is/are initiated 49624, during the period the cutting member is advancing 49626, and during the period the cutting member is retracting 49628, e.g., based on autonomous firing control algorithm 49608, as described herein). In an example, when the cutting member is advancing 49626 and hence pushing the tissue and increasing the load on the tissue, additional clamping force may be applied to the clamping jaw. The additional clamping force may be proportional to the increased load on the tissue. The additional clamping force may be utilized to maintain pressure/grip 49618 (e.g., constrain the tissue) and minimize tissue movement.

The continuous application of force may cause the clamping jaw to maintain pressure/grip 49618 on the tissue, which may include applying additional clamping force on the tissue during the firing sequence (e.g., based on autonomous clamping control algorithm 49606 as described herein). For example, the firing sequence may include multiple firing phases and the cutting member may pause (e.g., briefly) at the end of each firing phase. In such case, additional clamping force is applied to expel fluid from the cut tissue (e.g., for a pre-defined period) during the pause and the clamping jaw resumes advancing the clamping jaw after the pause.

The continuous application of force may cause the clamping jaw to maintain pressure/grip 49618 on the tissue, which may include progressively closing further during the firing sequence (e.g., based on autonomous clamping control algorithm 49606, as described herein). For example, when the cutting member is advancing and hence pushing the tissue and an increasing firing load is required to cut the tissue, the clamping jaw may be further closed progressively. The progressive closure of the clamping jaw may be proportional to the increased firing load. The progressive closure may help stabilize the tissue and hence reduce the firing load required to cut the tissue.

The smart surgical stapler 49604 may receive a second discrete signal associated with firing control operation (e.g., via a control circuit, as described herein). In an example, the second discrete signal may be initiated (e.g., via the control circuit) by healthcare professional's actuation of a firing control trigger. In an example, the second discrete signal may be actuated autonomously by autonomous clamping control algorithm 49606. The e.g., autonomous actuation may be in response to the completion of step Wait 49616. In response to the second discrete signal, a second continuous signal may be generated (e.g., via the control circuit) to cause a deployment operation (e.g., advancing 49626 a cutting member and retracting 49628 the cutting member to a starting position) based on autonomous firing control algorithm 49608.

Based on autonomous firing control algorithm 49608, the second continuous signal may cause a cutting member to advance a controlled manner. For example, advancement may accelerate to a pre-defined speed and maintain at that speed until it is sensed that there is no more tissue ahead of the cutting line and subsequently deaccelerate to a stop. Firing control algorithm(s)/control program(s) are described in greater detail in U.S. patent application Ser. No. 16/209, 416, titled METHOD OF HUB COMMUNICATION, PROCESSING, DISPLAY, AND CLOUD ANALYTICS, filed Dec. 4, 2018 and in U.S. patent application Ser. No. 16/209, 423, titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, the disclosure of which is herein incorporated by reference in its entirety.

Based on autonomous firing control algorithm, advancement of the cutting member may be adjusted autonomously. For example, advancement of the cutting member may be adjusted autonomously based on a measurement. In an example, control algorithm may cause the advancement of the cutting member to pause if a sensed firing load exceeds a pre-defined threshold. In some cases, the pause may last a pre-defined amount of time, before advancement is resumed. In some cases, the pause may last until a tissue load (e.g., viscoelastical load properties due to the tissue) measurement falls below an acceptable threshold, before advancement is resumed. In some cases, there is a max number of times advancement may be attempted to be resumed after a pause and if, a max number of attempts is reached, advancement may be completely stopped and manual intervention of a healthcare professional 49602, may be required.

In an example, control algorithm may cause the advancement speed of the cutting member to adjust based on force(s) (or load) sensed on clamping jaws. If a sensed firing load increases at rate that's above a predefined threshold, the advancement speed may be reduced for a predefined amount of time. After the predefined amount time elapses, the advancement speed may be increased to the previous advancement speed.

In an example, control algorithm may cause the advancement to completely stop if a maximum firing load (e.g., a maximum advancement force) or the maximum firing load is sensed more than a pre-defined maximum number of times. In an example, control algorithm may cause the retraction of the cutting member to completely stop if a maximum firing load (e.g., a maximum advancement force) or the maximum firing load is sensed more than a pre-defined maximum number of times.

Predefined settings may be used to control automation or discrete motions. The setup configuration of the surgical instrument may have a setting that instructs the surgical instrument to run fully autonomous to complete, run partially to a predefined step, or remain in discrete mode with limited or no autonomous action. A tiered system-based autonomy architecture may be implemented. A surgical instrument may come from factory set up for a full manual mode. The surgical instrument may enter an operating room (OR) and a surgical hub may establish a communication pathway to the surgical instrument. The pathway may be interrogated for speed and accuracy. If communication path is adequate, the surgical hub may instruct the surgical instrument about the level of autonomy that may be used in a surgical procedure. Specific break points may be established in an autonomous operation and the surgical instrument may pause and hold until a healthcare professional (e.g., a surgeon) or an OR personnel acknowledges the break and command the surgical instrument to continue. Breakpoints may be established based on individual healthcare professional's preferences and/or may use the AI collective data for common break points. Previous uses by a specific healthcare professional may be used to learn the healthcare professional's preferences and may allow the surgical hub to instruct the surgical instrument to set an autonomy level to a pre-defined setting. Detected issues with the device, previous procedure steps, patient biomarkers, or healthcare professional biomarkers, or surgical hub communications with the device may set the level of automated action the surgical instrument is capable of using.

An automated operation may be locked out based on detection of an incorrect situation. For example, adaptive close typically allow automatic action of the closure tube while the firing system is operating. if the closure system is near it limits or if it detects significantly early contact with tissue, the adjustment during firing may be disabled. The same triggers that control prevention of automation may adjust another system's automation.

Figure 9:
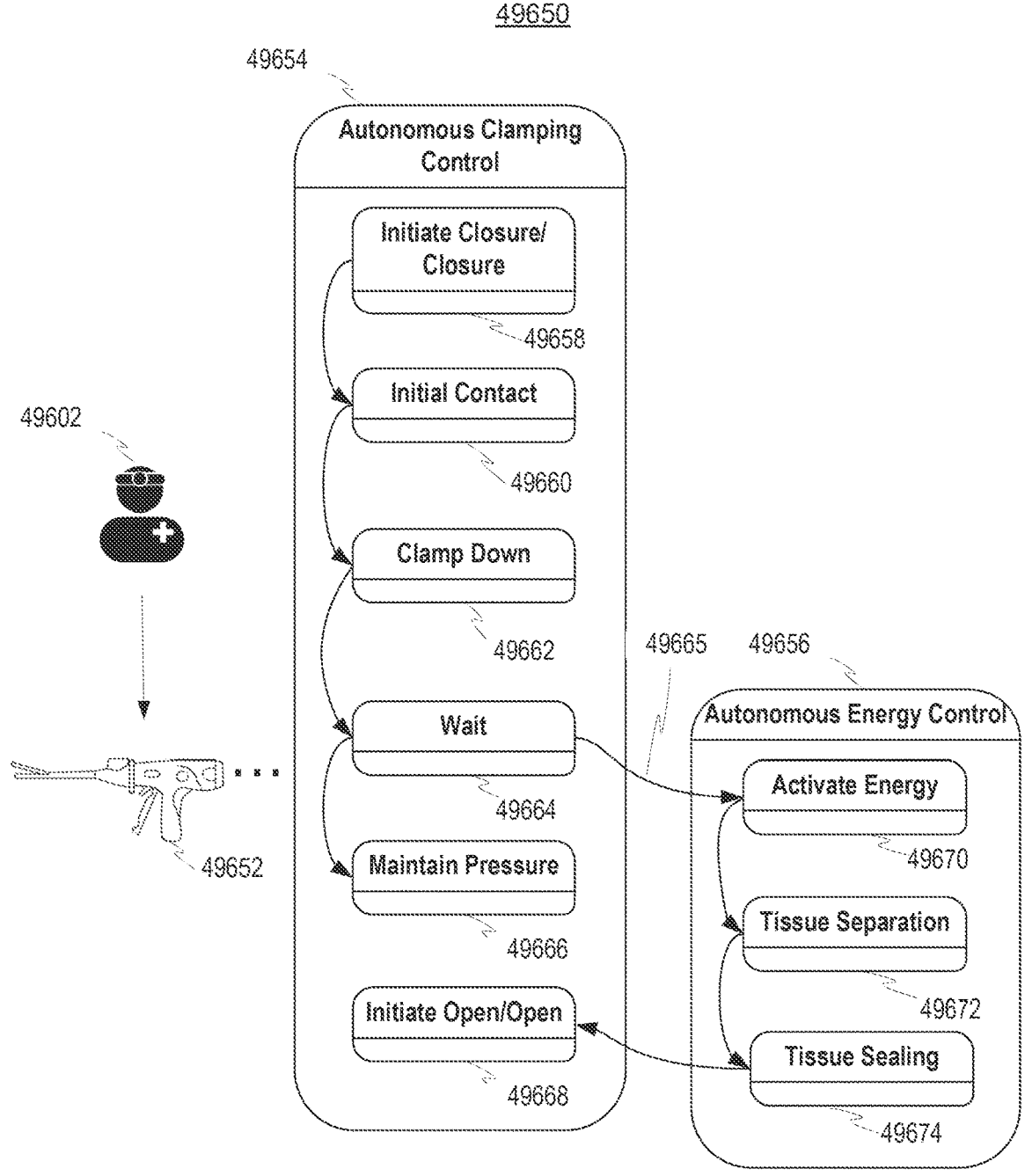
FIG. 9 illustrates an example autonomous operation of a surgical instrument.

FIG. 9 illustrates an example autonomous operation of a surgical instrument, 49650. The surgical instrument may be a smart energy device. Additional details about operation of a smart energy device are disclosed in U.S. patent application Ser. No. 16/209,453, titled METHOD FOR CONTROLLING SMART ENERGY DEVICES, filed Dec. 4, 2018, the disclosure of which is herein incorporated by reference in its entirety.

A smart energy device may be a harmonic device (e.g., an ultrasonic scalpel). An ultrasonic scalpel includes an upper blade (which may include or may be a tissue pad) is an inactive one, which helps in grasping tissue(s) and prevents the vibration energy from spreading further while a lower active jaw vibrates and denatures protein in the tissue(s) to form a sticky coagulum. The mechanical vibrations may be produced by the piezoelectric transducers embedded in the device (e.g., in the upper blade and/or the lower active aw) which convert the applied (e.g., produced) electrical energy to mechanical vibrations which are then transferred to the active blades for cutting or coagulation. The ultrasonic scalpel operates at a frequency of 55.5 kHz and has five power levels. Increasing a power level may increase cutting speed and decrease coagulation. Less power may decrease cutting speed and increase coagulation.

A smart energy device's (e.g., an ultrasonic energy device, such as an ultrasonic scalpel) operation may include clamping control and energy control. Clamping control may include control associated with one or more the following steps: initiating closure of a clamping arm/closure of a clamping arm, initial contact with a tissue, clamping down (e.g., to a pre-determined pressure), wait (e.g., for a pre-determined period during which tissue creep occurs), maintaining pressure (e.g., during energy generation), or initiating opening a clamping arm/opening a clamping arm. Energy control may include control associated with one or more the following steps: activate energy generation (e.g., by an energy blade), tissue separation (e.g., by an energy blade), or tissue sealing (e.g., by an energy blade).

A smart energy device 49652 (e.g., an ultrasonic energy device) may include a processor that is configured with one or more control algorithms for its autonomous operation, for example, as described in FIG. 5 herein. The smart energy device 49652 may be configured with a control algorithm associated with autonomous clamping control operation 49654. The smart energy device 49652 may be configured with a control algorithm associated with autonomous energy control operation (e.g., autonomous energy control algorithm 49656). The smart energy device 49652 may be configured with a control algorithm associated with the autonomous clamping control operation and the autonomous energy control operation. The autonomous clamping control algorithm 49654 may be associated with one or more steps, such as initiate closure/closure 49658 of a clamping arm, initial contact 49660 with a tissue, clamping down 49662 (e.g., to a pre-determined pressure), wait 49664 (e.g., before activating energy 49624), maintaining pressure 49666 (e.g., during energy generation), initiating opening a clamping arm/opening a clamping arm 49668 (e.g., after tissue sealing 49674 is complete). The autonomous energy control algorithm 49656 may be associated with one or more steps, such as activating energy 49670, energy generation for tissue separation 49672, energy generation for tissue sealing 49674.

The smart energy device 49652 (e.g., an ultrasonic energy device) may receive a first discrete signal associated with clamping control operation (e.g., via a control circuit). The first discrete signal may be initiated (e.g., via the control circuit) by healthcare professional's actuation of a clamping control trigger. In response to the first discrete signal, a first continuous signal may be generated (e.g., via the control circuit) to cause a continuous application of force (e.g., on a clamping arm) based on autonomous clamping control algorithm 49654.

Based on autonomous clamping control algorithm 49654, the continuous application of force may cause a clamping arm to initiate closure/closure 49658, make initial contact 49660 with a tissue, clamp down 49662 (e.g., to a pre-determined pressure), wait 49664 (e.g., before activating energy 49624), maintain pressure 49666 (e.g., during energy generation), initiate opening a clamping arm/open a clamping arm 49668 (e.g., after tissue sealing 49674 is complete).

The smart energy device 4965.2 may receive a second discrete signal associated with energy control operation (e.g., via a control circuit). The second discrete signal may be initiated (e.g., via the control circuit) by healthcare professional's actuation of an energy control trigger (or autonomous actuation by autonomous clamping control algorithm 49654, e.g., in response to the completion 49665 of step wait 49664). In response to the second discrete signal, a second continuous signal may be generated (e.g., via the control circuit) to cause a deployment operation (e.g., energy generation for tissue separation 49672 and energy generation for tissue sealing 49674) based on autonomous energy control algorithm 49656.

Based on autonomous energy control algorithm 49656, the second continuous signal may cause the energy blade to generate energy to separate the tissue. For example, the energy blade may generate energy of a first predefined power level (e.g., a higher level) that is sufficient to separate/cut issue.

During the tissue separation, the tissue content may be monitored/measured to determine whether to adjust the energy generation to seal the tissue. For example, ratio of collagen to elastin of the tissue may be measured (e.g., continuously during tissue separation). If collagen is measured to have been denatured below a predefined threshold, the energy blade may generate energy of a second predefined power level (e.g., a lower level) that is sufficient to seal the tissue.

During the issue sealing, the tissue content may be monitored/measured to determine whether to stop the energy generation (e.g., after tissue sealing is complete), e.g., to avoid damaging the upper clamping arm. For example, amount of the tissue may be measured (e.g., continuously during tissue sealing). If it is detected that no tissue is between the clamping arm and the energy blade, energy generation is stopped.

The clamping pressure between the active blade (e.g., the energy blade) and inactive blade (e.g., the clamping arm) may impact the tissue separation/tissue sealing (e.g., transection of tissue/vessel sealing) and/or may alter the frequency and/or impedance and/or cause blade fatigue. The clamping pressure may controlled (e.g., manually controlled) by the healthcare professional and may (e.g., drastically) alter the intended results. As described herein, allowing the smart energy device to autonomously control the clamping pressure and the amount/level of energy applied based on the tissue/vessel or intended action may improve consistency to therapeutic treatment and/or minimize trauma to unintended areas.

Based on autonomous clamping control algorithm 49654, the continuous application of force may cause a clamping arm to autonomously control grasping and tissue manipulation. In the case of tissue manipulation, pressure between jaws may be controlled to not damage tissue. Clamping pressure may be increased or decreased as healthcare professional grasps and moves tissue. When the healthcare professional moves the tissue, additional loads can be placed on the tissue as it moves/stretches, and/or loads on the tissue may reduce and the tissue fall out of the jaws. In such case, damage to the tissue may be caused, distractions and/or delays in procedure may be caused. The type of tissue the smart energy device is about to grasp (e.g., via sensor(s) of the smart energy device and/or visual detection data of the tissue from an image system/scope, as described herein) may be identified. When a scope/smart energy device detect the movement, direction, and load imparted on the tissue, the clamping pressure ma be increased/decreased based on autonomous clamping control algorithm 49654.

The use of the visual feedback through a scope in conjunction of a smart energy device's control algorithm for monitoring impedance (e.g., autonomous energy control algorithm 49656) may be used to alter the clamping pressure and energy levels delivered to the smart energy device. The scope and the smart energy device 49652 (e.g., via the response of both systems) may control the therapeutic treatment (e.g., as opposed to the control by the healthcare professional). In an example, a bi-polar energy device may rely on clamping pressure and heat for therapeutic treatment and the approach described herein for use of visual feedback and control algorithm for monitoring impedance may be utilized for maintain the clamp pressure based on tissue type and/or vessel size, e.g., to optimize sealing.

Autonomous operation of a system actuation based on the detection of the maximum combined forces applied to the tissue may be implemented to minimize inadvertent tissue trauma during interaction. The clamping force may be limited by the tangential pull force and the clamping combined to limit tearing. The loading on tissue may be autonomously calculate based On the cumulative loading of multiple devices and this information may be used to influence the activation of an additional device. In an example, two graspers may be used to hold tissue in position for an energy transection (e.g., tissue transection with an energy device). Tissue load may be calculated based on the loading between these graspers. Tissue load during energy activation for energy generation) may influence the quality of the seal. The energy activation level (or energy generation level) may be adjusted based on the calculated tissue load. Subtle autonomous adjustments to the grasper positions may be made to alter the tissue loading, e.g., reduce loading for improved seal quality.

Haptic feedback may be provided to a healthcare professional (e.g., a surgeon) when autonomous operation deviates from planned procedure steps and locations. For example, ortho style geo-fencing around tumor resection in solid organ may be implemented. Creation of liver resection plane may be implemented with respect to lobe/zone of tumor being removed.

FIG. 10 is a flow chart of an example autonomous operation of a surgical instrument (e.g., a smart surgical device), 49680. At 49682, a first discrete signal associated with clamping control was received. For example, the smart surgical device may be a smart surgical cutting device or a smart surgical energy device. The first discrete signal may be associated with initiating closure of a clamping jaw. The first discrete signal may be triggered by a healthcare professional.

At 49684, a first continuous signal to cause a continuous application of force based on a first autonomous control algorithm, in response to the first discrete signal, is generated. For example, the continuous application of force may be adjusted autonomously based on at least a first measurement.

For example, the smart surgical device may be a smart surgical cutting device. The continuous application of force may be applied during one or more of the following steps: initial contact, clamping down, wait, maintaining pressure, or relieving pressure. The first measurement may be one of the following: a load on a clamping jaw at a first contact with a tissue, a load on the tissue when clamping down, and a tissue measurement that indicates presence of a rigid object.

For example, the smart surgical device may be a smart surgical energy device. The continuous application of force on a tissue may be applied during one or more of the following the clamping control: initial contact, clamping down, wait, or maintaining pressure. The first measurement: may be a position of a tissue between a clamping arm and an energy blade.

At 49686, a second discrete signal associated with a deployment operation is received. For example, the smart surgical device may be a smart surgical cutting device. The deployment operation may be advancing of a cutting member and retracting of the cutting member.

For example, the smart surgical device may be a smart surgical energy device. The second discrete signal may be associated with initiating a firing sequence. The second discrete signal may be triggered by a healthcare professional or autonomously. The deployment operation may be generation of energy.

At 49688, a second continuous signal to cause the deployment operation based on a second autonomous control algorithm, in response to the second discrete signal, is generated. For example, the deployment operation may be adjusted autonomously based on at least a second measurement. The second measurement may be a ratio of collagen to elastin in the tissue.

Scope function may be autonomously controlled, e.g., based on tissue parameter(s) and/or healthcare professional-defined parameter(s). In the case of focusing; zooming function, a focal point may be adapted autonomously, e.g., based on monitoring end-effectors' current primary action and/or current interaction location. In the case of repositioning to control field of view, repositioning may be controlled to follow actions of a healthcare professional's instrument (s). Repositioning may be controlled to be based on a next step associated with a surgical procedure plan or an indication of a next step by the healthcare professional. Repositioning may be controlled to balance between two separate imaging sources to maximize field of view. In isle case of adjustment of imaging configuration based on situational awareness, adjustment may be made to change from visual light to a multi-spectral wavelength or may be made to change back (e.g., based on the job(s), outcome(s), constraint(s) (JOC) at hand). In the case of monitoring of imaging outside of the displayed field of view and correlations of objects that are detected to identify potential interactions, displayed field of view may be digitally limited to a level smaller than the CMOS arrays are capable of detecting. A mesh of detectors may be used to look for object(s) and determine their location(s) and potential for collisions/interactions. In the case of signaling undesirable outcome not currently visible on the main screen, a popup (e.g., in a corner of main monitor) may be used to show a detected leak currently not visible (e.g., leak currently not visible clue to off screen or leak currently not visible in current visual spectrum. For example, pancreatic leaks may be clear and very difficult to perceive, and alternate visualization technique(s) may be used to detect these and the healthcare professional may be alerted accordingly.

Surgical device movement controls (e.g., articulation) may be modified autonomously based on orientation of the surgical device on a healthcare professional monitor. Video analysis may be performed to determine a position of an end effector relative to the healthcare professional monitor. The healthcare professional controls may be adjusted based on the screen orientation of the end effector. For example, if the healthcare professional thinks in terms of left vs right, she/be may think in terms of left and right relative to the monitor screen. In such case, the method of movement control modification described herein may mitigate any confusion that may exist when handling of end effectors is for awkward positions. be method of movement control modification as described herein may be relative to the monitor being viewed by the healthcare professional (e.g., the left button on the monitor may move the end effector left). The method of movement control modification may be irrespective of the orientation of the surgical device's healthcare professional interface. In an example, a healthcare professional may place an endocutter in a patient and may handle the device in unknown position relative to the device's shaft. Real time video analysis may identify the end effector with its anvil facing up or down. The analysis may determine the end effector's position relative to the healthcare professional monitor (e.g., on the left or right of the monitor). A surgical hub (e.g., a control tower) may communicate to endocutter to adjust the controls of the endocutter (e.g., for a consistent healthcare professional experience). In such manner, the healthcare professional may operate articulation with minimal confusion (e.g., relative to the healthcare professional's view, such as left articulation button corresponding to going left and right articulation button corresponding to going right).

A detection mechanism may be implemented to monitor where the surgical device may be located. Choices may be provided regarding notifying information about a surgical device. The notified information may indicate how to handle the surgical device. For example, the information may include instructions regarding how to disconnect the surgical device and/or how to dispose the surgical device. Disposing of substances of very high concern may be regulated by one or more of a regional authority, a national authority, or a local authority. For example, The Batteries Directive of the European Union regulates the manufacturing and disposal of batteries and accumulators in the European Union to protect human health and the environment from hazardous substances such as mercury and cadmium. Similarly, Waste from Electrical and Electronic Equipment (WEEE) is another directive that focuses on waste electrical and electronic equipment or e-waste. WEEE directive's focus is on preventing the creation of WEEE, contributing to the efficient use of resources and the retrieval of secondary raw materials through re-use, recycling, and other forms of recovery, and improving the environmental performance of everyone involved in the life cycle of EEE.

Choices of how to notify to a healthcare professional about handling a surgical device that may include substances of very high concern, and how to disconnect and dispose such surgical devices may help adhere to the sustainability of directives for a manufacturer (e.g., the manufacturer of the surgical devices). A surgical system may be adaptable to additions based on, for example, the geographic location or a country. The surgical system may be updated and/or directives may be provided as they become available.

A surgical hub may provide instructions for disposing off batters, electronics, and/or substances of very high concern (SVHC) based on location-specific ordinances. In an example, a surgical hub may adapt to a predetermine disposal system. The disposal system may be country-specific and/or locality-specific wherein the surgical device or the medical facility (e.g., a hospital) may be located. In an example, the surgical hub may determine its geolocation. Based on the geolocation, the surgical hub may determine the country-specific, the province-specific or state-specific, and/or the locality-specific ordinances for compliance.

In an example, batteries may be separated and placed into a battery waste stream. For example, a surgical hub may direct the operating room personal about the relevant stream for example, depending on the device and the battery chemistry.

In an example, a surgical hub may have access to a surgical device's bill of materials (BOM). Based on the surgical device's BOM, the surgical hub may perform a check (e.g., a periodical check) for any updates to the safety data sheets (e.g., material safety data sheet (MSDS) or pathogen safety data sheet (PSDS)) for any updated disposal instructions. The surgical hub may perform check over the Internet. The surgical hub may scan a manufacturers database to determine the latest directives about the materials associated with a surgical device. A surgical hub may provide instructions a health care provider (e.g., an OR associate) about how to being the recapture of components for reclamation.

A surgical hub may determine geolocation and use the determined geolocation to determine the proper disposal instructions associated with a surgical device. The surgical hub may use the geolocation for determining region-specific and/or country-specific cleaning and sterilization protocols. In an example, the surgical hub may use a surgical device's device code to determine its location. In another example, the surgical hub may use global positioning system (GPS), network, hospital identifier, a manufacturer's cloud-based system to determine the location of the surgical device. In another example, the surgical hub may use the internet protocol (IP) address and/or software license to determine the location of the surgical device. In an example, the surgical hub may use the airport codes to determine the location of the device. The mechanism by which the location may be determined may be healthcare professional selectable. In an example, the surgical device (e.g., the surgical EEPROM may be coded with region-specific and/or country-specific information. In an example, a surgical device may determine location as a part of initialization check by checking settings (e.g., field service settings).

In an example, disposal bins with smart scanning of surgical devices or components used in the surgical device may be provided for proper disposal. Specific disposal bins may be provided for disposing off various categories of disposable surgical devices and/or components in the surgical devices. A surgical device and/or the component may be matched with a disposal bin for disposing off a surgical device or a component into proper disposal streams. In case a mismatch between a surgical device or a component and a disposal bin is found, a healthcare provider (e.g., and OR associate) may be notified of the mismatch. In an example, the disposal bins may have near-field communication (NFC) or radio frequency identifier (RFID) readers to track various types or surgical devices and/or components being dropped into those disposal bins. In an example, surgical devices with NFC or RFID type chips may be checked, for example, when the devices are dropped into a disposal bin to ensure proper placement in a disposal stream.

Systems and/or devices for smart disposal may be provided for cooperative interaction between one or more healthcare professionals, one or more disposal bins, and/or one or more surgical hubs. The disposal bins may be wired or wirelessly in communication with the one or more surgical hubs. In an example, disposal bins may communicate with a healthcare professional regarding the type of disposal that may occur or may be expected to occur between a disposal bin and a surgical device or a component to be disposed. The communication may be direct or via the surgical hub or an application. In an example, mini display on a disposal bin may be provided to communicate disposal instructions to a healthcare professional.

In an example, information and/or signals associated with a smart disposal bin may match with the information and/or signals associated with a surgical hub healthcare professional interface. In an example, an indication (e.g., in the form of LED lights or other means of communication) may be provided to indicate a match or a no match between the signals on a smart disposal bin and signals on hub UI. In an example, bins may be provided for disposal, reclamation and/or reuse. Each of the bins may have green, blue, and/or an orange color codes. A surgical hub display may communicate the type of disposal for each surgical device or component a healthcare professional may be handling. The surgical hub display may indicate a green light for a device to be disposed, and the light on the green bin may begin to flash or light up. In an example, a disposal bin may wait for a surgical device to be disposed. When the surgical device is dropped into the disposal bin, and the RFID scanner detects the correct device, the light may stop flashing and the surgical hub may indicate a confirmation message that disposal of the surgical device was successful. If the healthcare professional drops the surgical device in a wrong disposal bin, the disposal bin may flash red, or warning light and the surgical hub display may indicate an error indicating, that the disposal of the surgical device was not successful.

In example, a surgical hub healthcare professional interface may be aware (e.g., actively aware) of status of disposal bins. The surgical hub may cross-check (e.g., actively cross-check) instructions with components in the disposal bins. In an example, a surgical hub may provide instructions (e.g., real-time instructions) for disassembly of surgical devices. For example, the surgical hub may provide the instructions we it may detect surgical devices and/or components being placed in the disposal bins. In an example, the surgical hub may keep track of a checklist of what is to be disposed off in a disposal bin against what is placed in the disposal bin.

A surgical hub may account for lost or missing devices during disposal of a surgical device and/or a component. In an example, a surgical hub may be aware of surgical devices and/or components that may be used during a surgical procedure, and smart disposal bins may cross check that each of the surgical devices used in a surgical procedure is accounted for during disposal to confirm lost or missing devices.

Disposal bins and/or one or more surgical hubs may communicate the disposal information with other hospital systems. In an example, the disposal bins and/or one or more surgical hubs may communicate with a healthcare facility inventory management system. In an example, cross checks may be made between the expected surgical devices that may be used in a surgical procedure with the actual surgical devices that were used and disposed of. Such comparison information may be communicated with the healthcare facility inventory management system.

In an example, disposal bins and/or one or more surgical hubs may communicate the disposal information with the cleaning staff of the healthcare facility. The disposal information may include information about cleaning and/or disposal unit within the healthcare facility, so they know what to expect when disposed devices are received. In an example, the disposal information may communicate with the cleaning staff of the healthcare facility that one or more disposal bins are full.

Smart disposal bins, for example, with device ID mechanisms, may collect surgical device data as the surgical devices and/or components are dropped into the disposal bins. For example, the data collected or some of the data collected may be stored on the surgical devices without communicating it with the surgical hub. In an example, smart disposal bins may scan devices and extract device data as they are dropped into the bins. The smart disposal bins may communicate the collected data with a surgical hub or a manufacturer's cloud system. In an example, smart disposal bins may connect to the surgical devices via RFID, NFC, etc. In an example, smart disposal bins and/or the surgical devices may interact with a manufacturer's cloud system via a gateway device.

In an example, an application on a mobile device (e.g., a phone application or a tablet application) may be used with device ID mechanisms and may be used to gain access to a surgical hub or a manufacturer's cloud-based data systems.

In an example, cleaning and/or sterilization staff may utilize a mobile device (e.g., a phone or a tablet) application with ability to scan and ID devices. The application may be integrated with the surgical hub networks for full interconnectivity, or when the surgical hub is not available, connect to a manufacturer's cloud site to gain access to device cleaning and sterilization protocols. Protocols may be communicated to the healthcare professional through the mobile device. Device ID, by way of NFC, RFID, BLE, etc. may be used to automatically extract device data and upload t to the manufacturer's cloud system.

In an example, an application (e.g., a portable application) may be provided on a mobile device with download and upload ability to accesses cleaning and/or sterilization protocols. The mobile device may utilize one or more of the following device identifying mechanisms: a QR code, a BLE connection, an NFC, or an RFID.

In an example, the application may be directly connected to the manufacturer's cloud system. Such an arrangement may be utilized in case of healthcare facilities that may not have access to a surgical hub. An access to surgical device cleaning and/or sterilization protocols may be provided. Step by step instructions about the cleaning and/or sterilization may be provided to healthcare professionals.

In an example, an application may utilize location information to provide country or region-specific cleaning and/or sterilization protocols and methods. The application may provide location services. The location may be automatically detected by using mechanisms as described herein or specified while setting up an account associated with the use of the application. The application may auto-connect to a manufacturer's customer service or a call center for help.

In an example, the application (e.g., alternatively or additionally may be connected to a surgical hub system. The application may have special permissions (e.g., limited permissions) with surgical hub connectivity. For example, cleaning and/or sterilization staff may have limited access or no access to a portion of surgical hub system. The access may be limited to the cleaning and/or sterilization related information. The application may communicate with interconnected hospital systems, for example, for OR system and/or inventory tracking, etc.

The application may communicate with one or more sterilization groups to inform them about the upcoming tasks they may need to perform. For example, cleaning staff personnel in OR may scan surgical devices while disassembling or disposing them. In an example, when a device intended to be sterilized is scanned, the sterilization group (e.g., in the same healthcare facility location or in a different healthcare facility location) may be notified of the incoming devices.

The application may be utilized to identify or confirm lost and/or missing surgical devices. A surgical hub may track surgical devices used during surgical procedures. The application may scan each of the surgical devices during cleaning procedures and may confirm that each of the surgical devices have been accounted for. The application may confirm disposal (e.g., proper disposal) when application is in communication with a smart disposal system. The application may notify maintenance when equipment is ready for service Data associated with a surgical device may be autonomously uploaded to a cloud system. The data upload may be initiated during device cleaning and/or sterilization. One or more surgical devices may store the surgical data associated with surgical devices throughout a surgical procedure. In an example, the surgical data may be stored on the device, for example, when connectivity with a surgical hub is not available. The surgical data may include device motor data, failures, error codes, etc.

In an example, surgical devices may nave limited or no connectivity with a surgical hub. In an example, the surgical devices may not have surgical hub to collect data associated with surgical devices.

Surgical device data may be extracted from the surgical devices when they are scanned in for cleaning. The data extraction may be performed using BLE, RFID, NFC or other communication protocols.

Surgical device data processing may occur autonomously. Such processing may not be accessible to cleaning and/or sterilization staff. Surgical device data processing may occur autonomously once a surgical device is connected.

Surgical device data may be sent from an application (e.g., an application on a mobile device) to a surgical hub system or directly to a manufacturer's cloud system. In case of manufacturer's cloud, a gateway device may be used between surgical devices and a manufacturer's could system.

Intra-operative autonomous device evaluation, adjustment or refurbishment may be provided. Surgical devices used over a period of time in surgical procedures may degrade in performance or be damaged in a way that they do not perform optimally but may still be usable. Such surgical devices may be autonomously refurbished within a surgical procedure.

In an example, harmonic teflon pads may be made available and replaceable intraoperively. A teflon pad replacement cartridge tool may be provided for longer than usual surgical procedures (e.g., extremely long surgical procedures), or in situations in which teflon pads are most prone to damage. The harmonic device may exit the patient, and autonomously be inserted into this tool where the damaged pad is removed from the device and a replacement pad is positioned into place.

In an example, as the teflon pads are damaged, if they cannot be replaced, a mechanical clamp arm adjustment may be made to raise or lower the pivot of the clamp arm and optimize the gap setting.

A surgical device's operational output of outcomes may be mapped back to the functional degradation of a part of a surgical device. The outputs may be used as an input to a system to indicate to the healthcare professional that the current remaining or expected performance and its degradation relative to original. The automated monitoring and comparison may be used to trigger updates to control programs and/or replacement or swapping out of parts or aspects of the device to revert the device's performance to its original level. In an example, au RE bipolar surgical device electrode conductivity or contamination may be used to trigger or indicate when the jaws of the surgical devices are to be cleaned. Cleaning of the jaws may be performed autonomously and/or intraoperatively. If the cleaning of the jaws does not result in a desired improvement or the degradation of the functionality is not reverted to a desired level, a selectively replaceable portion may be exchanged or replaced autonomously and/or intraoperatively. Such replacement may be performed, for example, when the system measures inappropriate resistance in an intentional short activation when the device is inserted or removed from the trocar. Data collected over a period of time from the continuous and autonomous monitoring and/or checking of the surgical device and the automatic comparison may be utilized for providing a better understanding of the surgical device.

Figures 11A, 11B:
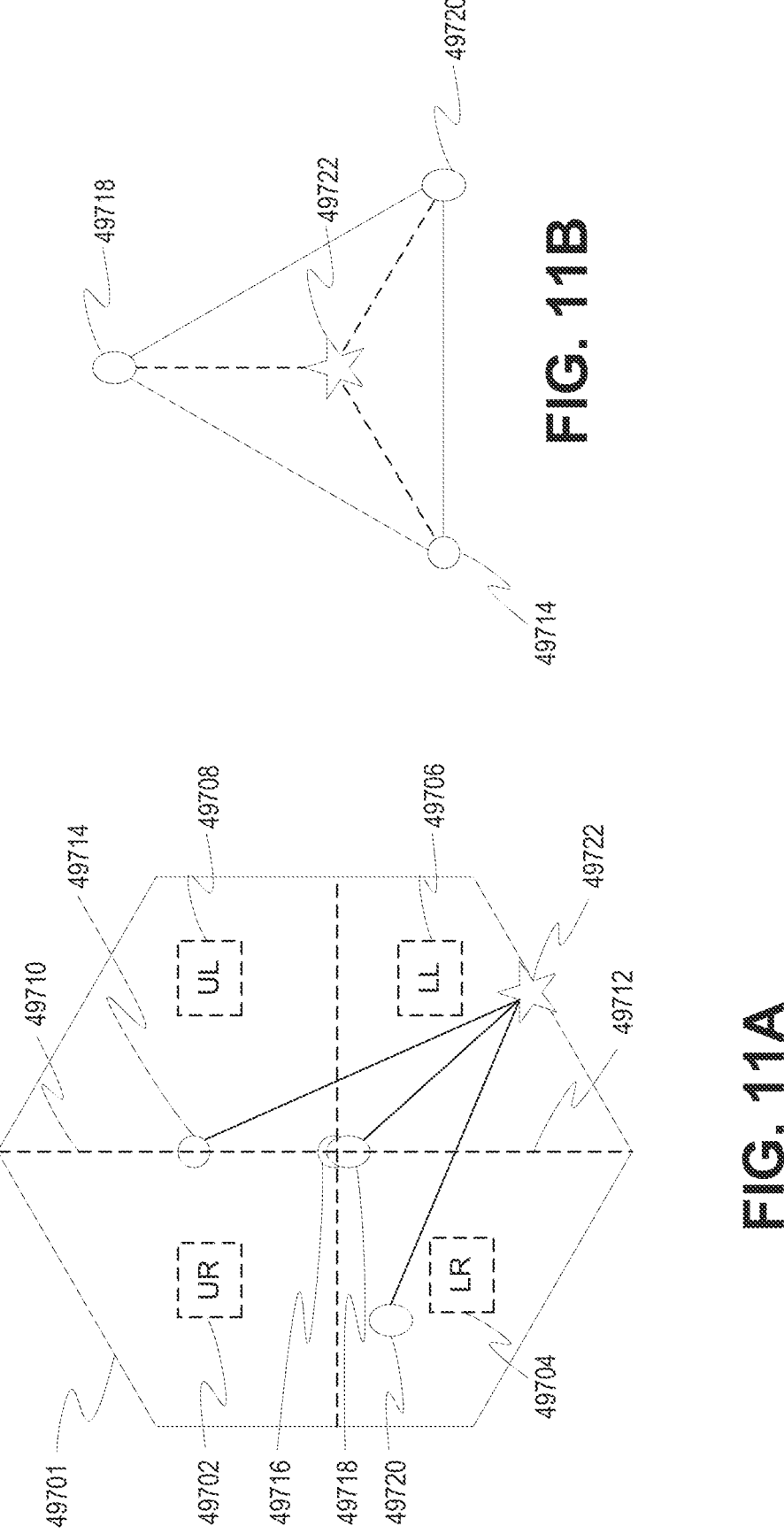
FIG. 11A through FIG. 11B illustrate example trocar placements.

In laparoscopic surgery, trocars may be utilized to seal the skin openings, while permitting entry and removal of surgical instruments needed for a surgical procedure. FIG. 11A and FIG. 11B illustrate example trocar placements during, a surgical procedure. As illustrated in FIG. 11A, a shape 49701 represents the abdomen of a patient's front. The shape 49701 is divided into upper right quadrant (UR) 49702, upper left quadrant (UL) 49708, lower right quadrant (LR) 49704, and lower left quadrant (LL) 49706, with umbilicus 49716 in the center. A midline consisting of an upper midline 49710 and a lower midline 49712 divides the shape 49701 into equal left and right halves. An oval shape 49718 overlapping, with umbilicus 49716 represents a location of an incision for a laparoscope's trocar port. An oval shape 49720 in the LR area represents a location of an incision for a harmonic energy device's trocar port. A circle shape 49714 on the upper midline 49710 represents a location of an incision for a grasper's trocar port. A star shape 49722 represents a location of a target anatomy (e.g., sigmoid colon in a laparoscopic sigmoid colectomy). 49718, 49720, 49714 represent surgical choices of incision location for an incision for a trocar port. Solid lines between 49720 and 49722, between 49718 and 49722, between 49714 and 49722 represent the spatially relationships among the laparoscope, the harmonic device, the grasper when the three of them are all pointed at the target anatomy 49722 during a surgical procedure. Such spatial relationships represent a spatial arrangement of laparoscope and two surgical instruments that provide sufficient visibility of the surgical instruments as the three of them are working on the target anatomy. Such arrangement may be referred to as triangulation.

FIG. 11B shows a field-of-view perspective of the spatial relationships among the laparoscope, the harmonic device, and the grasper when the three of them are all pointed at the target anatomy 49722 during a surgical procedure. As such, the sight of the harmonic device and the sight of the grasper are maximized when the three of them are both pointed at and working on the target anatomy 49722 during a surgical procedure.

Instrument (e.g., surgical instrument) may perform autonomous action(s) during reloading, repositioning, and/or cleaning for completion of an action (e.g., a surgical action). For example, autonomous repositioning of an energy device may be per during cleaning. Keeping the jaws and/or the blade clean and/or free of debris throughout a surgical procedure may prevent tissue and/or debris build-up, which may lead to unintended generator error(s) that may require troubleshooting (e.g., additional troubleshooting). A system (e.g., within the energy device or with a surgical hub linked to the energy device) may autonomously monitor for when the jaws require cleaning and may retract the energy device from a surgical site to be cleaned. After the jaws are cleaned, the energy device may autonomously return to the position (e.g., the exact position) the device was at prior to being cleaned.

A system (e.g., a system within a surgical instrument or within a surgical hub linked with the surgical instrument) may use contextual information (e.g., contextual information gathered from additional surgical hub inputs) to determine a time (e.g., a most appropriate time) during operation to remove (e.g., from a surgical site) and clean. For example, a surgical instrument may be automatically removed from a surgical site and cleaned during a monotonous mesentery or momentum separation. If a healthcare professional (e.g., a surgeon) is dissecting (e.g., carefully) a critical structure, a risk (e.g., a risk of tissue/debris build-up) may be alerted to the healthcare professional and the healthcare professional may be allowed to continue using the surgical instrument.

A number of remaining steps (e.g., surgical steps) and/or a remaining distance of dissection may be used to determine when to clean a surgical instrument. The determination may be based on the surgical instrument performance and/or impact (e.g., anticipated impact) of interruption of progress (e.g., momentum of surgical progress)

A stapling device may be autonomously repositioned (e.g., after reloading of cartridge). A stapling device may require reloading during a surgical procedure (e.g., based on a length of area that is stapled). After the stapling device is fired it may be detected that another reload is required and the stapling device may autonomously retract from a surgical site, e.g., to a position that was easily accessible for the reload. After the reload, the stapling device may return to a position (e.g., an exact position where the stapling device was prior to the reload). The stapling device may identify a reload (e.g., a required reload) and may confirm the reload (e.g., confirming the required reload is correct).

An endocutter reload tray may be positioned such that a system (e.g., a system within the endocutter or a surgical hub) may autonomously remove the endocutter from a patient and may autonomously reload the device. Proper positioning of the reloads may ensure that arms (e.g., robotic arms holding the endocutter) may be moved without interfering with other arms (e.g., robotic arms) or obstructions. An optimal reload tray position may be determined, e.g., based on a surgical procedure type, devices installed, a healthcare professional's (e.g., a surgeon's) preferred arm positions, etc. A system (e.g., a system associated with a surgical hub) may position the reload tray, and/or may direct assistants) for proper positioning. The reload tray may be attached to an unused robotic arm and the tray may move to a position (e.g., a most appropriate position) when needed. The in-room (e.g., operating room) monitoring of a surgical hub may be used to determine an exact location of a holding structure relative to a robotic arm trocar holding location. In such manner, the robotic arm may be positioned in a location (e.g., a best location) for reload automatically. If robot arm(s) that can only retract the instrument to a point where it is still within the trocar. In such case, a healthcare professional (e.g., a surgeon) may be required to remove the instrument from an instrument driver (e.g., a tool driver) and may manually remove one cartridge and load another. Once a newly loaded instrument (e.g., tool) is re-attached to the instrument driver (e.g., the tool driver), the robotic arm may (e.g., then) finish the automation of motion for repositioning. In such example, the automatic motions may be retraction and/or re-positioning and loading a new cartridge may be automated or may be performed manually.

Registration to marker(s)/instrument(s) may be for tracking/repositioning. Positioning of instrument/tools may be difficult to perform because it may require tracking of an anatomy (e.g., an underlying anatomy) and/or may require maintaining registration to the underlying anatomy. Maintaining registration to the underlying anatomy may allow the instrument/tool to register its position in a space (e.g., a body cavity space) prior to retracting. By identifying markers/ anatomical structures, the instrument/tool may reposition itself back into its previous position. For example, the instrument/ tool may account for any patient movement/ anatomy movement and may reposition itself to its previous point (e.g., adjusting to compensate for the movement). The instrument/tool may use other instruments/devices/tools as markers for registration in a space (e.g., a body cavity space) during repositioning when the instrument/tool is being cleaned or reloaded.

Virtual access boundaries for large motion automatic reposition(s) may be implemented. A surgical instrument may be controlled to autonomously reposition obstructions during navigation to a treatment site. A surgical procedure may require manipulation and dissection of a tissue, organ(s) and/or repositioning obstruction(s) to gain access to the treatment site. For example, a vision system, an imaging system, and an AI control may be used to identify a targeted area, obstructions and may autonomously control the graspers/retractors to move the obstructions, e.g., to gain the most access. In such case, the required access needed may be visible or determined based on the healthcare professional's (e.g., the surgeon) knowledge of the volume of space required for an instrument to pass and/or gain access and/or size of resection that the healthcare professional was planning to remove. In some examples, pre-operative imaging (e.g., imaging associated with previous surgical procedures, such as gold standard procedures), patient biometrics, and/or the scope may be used to determine optimal control of organ/tissue/obstruction repositioning, such as determining how much/far organs/tissue/obstructions may be moved to minimize trauma.

A surgical device's range of motion may be autonomously controlled. Virtual boundaries may be created for a surgical device's range of motion (e.g., to constrain the range of motion/articulation). For example, virtual boundary/structure may be created for each surgical instrument/device autonomously. Such virtual boundary/structure may constraint a healthcare professional's movement(s) to a certain volume (e.g., to serve as a guide to the healthcare professional, which may identify if she/be needed to reposition and may protect the patient from the instrument/device making unattended contact, which may damage unintended areas). Such virtual boundary/structure may be shown on a monitor (e.g., a healthcare professional's monitor) and/or may restrict the movement(s) of the instrument; device in areas outside of the intended treatment area.

A fire-and-forget system operation (e.g., of a surgical instrument) may be implemented. The fore-and-forget system operation may be sequential. The fore-and-forget system operation may be based on healthcare professional selected input and/or autonomous instrument control. For example, autonomous fire-and-forget system operation of monopolar devices may be implemented. Monopolar devices may use an electrosurgical generator, which may have two primary Sanctions, such as cut and coagulate settings. The cut function may use unmodulated continuous waveform. The unmodulated continuous waveform may result in a flow of low energy electron and may generate minimal smoke production during tissue cutting. The coagulation function may use modulated interrupted waveform. The modulated interrupted waveform may be associated with a high energy electron flow and may generate more smoke production with high temperature but better hemostasis. A monopolar device may have an ability to use a continuous and/or mix/blend current to dissect tissue to achieve hemostasis. Autonomous selection of cut, coagulate and/or a blended energy may be applied, e.g., based on detection of an imaging system and/or identification of tissue type(s). An amount of energy and a direction of energy may be autonomously controlled, e.g., based on tissue and/or surrounding structures.

For example, autonomous fire-and-forget system operation of a hi-polar and/or an ultrasonic device may be implemented. Bi-polar/ultrasonic devices may be used for dissection and/or tissue-sealing and hemostasis. Automation of the firing may be performed to control a speed to close the jaws, to control clamp pressure required (e.g., based on a tissue/vessel type), to control wait time of compression, and/or to control the energy level(s) that are applied. Monitoring through a scope device may be used to verify/confirm and/or may be used to modulate or adjust.

For example, autonomous fire-and-forget system operation of combo energy devices may be implemented. Combo energy device may autonomously control a type of energy that is applied based on the tissue type and/or vicinity to surrounding structure(s), e.g., to minimize unintended tissue damage. Visual detection through a scope device and identification of surrounding, structures may be used to control the energy the device is configured to (e.g., is able to) activate.

For example, autonomous fire-and-forget system operation of stapling devices. Automation of the firing may be performed to control a speed to close the jaws, to control clamp pressure required (e.g., based on a tissue/vessel type), to control wait time of compression, and/or to control a speed of the motor to drive the firing mechanism.

Autonomous tire-and-forget tissue tension monitoring may be implemented. Sealing and/or transecting vessels/ tissue/organs when using an energy device and/or a stapling device may be altered, e.g., based on tension under a targeted area/zone that is being fired on. Automatically monitoring the tension under a targeted area/zone may be used prior to activating the firing of the device. In the case of harmonic devices, bench top testing (e.g., bench top testing used to submit for regulatory approval) may indicate that sealing of vessels is performed under an axial tension of 50 g on the vessel. To optimizes a system (an autonomous fire-and-forget system), the jaws may apply a 50 g axial load on the tissue for sealing.

Tissue tension may be manipulated as a variable in sealing. Subtle device movement(s) may be used to increase/ decrease tissue tension, e.g., based. On sealing/transecting/ speed prioritization. For example, a tissue may be detected as mesentery. The energy device/instrument may prioritize a faster speed and may increase tension during energy activation. in the case of increasing speed of transection, the energy device/instrument may apply a movement (e.g., a subtle movement) to lift an end effector (e.g., orthogonally in relation to jaw clamping). Such lift may be performed during the entire energy activation or for a portion of the energy activation, e.g., based on the speed required. Such movement may be subtle (e.g., imperceptible to the health-care professional).

In an example, a tissue may be detected as a critical vessel. The energy device/instrument may prioritize seal quality and may decrease tension during energy activation. In the case of prioritizing seal quality, tissue tension may be reduced (e.g., minimized). Reduction of tissue tension may be performed by monitoring end effector joint loads and/or tissue characteristics through visualization and moving (e.g., subtly) the end effector away from direction(s) of higher load. Tissue tension may change through the sealing cycle and subtle movement(s) may be performed throughout seal-ing, e.g., to ensure minimal tension.

One or more triggers may be used to assess tissue tension. In examples, visual analysis of a tissue may be performed and changes in tissue coloration adjacent to jaws may be a trigger. Visual analysis of width of a tissue may be per-formed and high tension may be indicated by a narrow tissue, which may be a trigger. Perfusion analysis may be performed, and decreased perfusion may be a trigger/indi-cator that excess tension is being applied. Device loading may be monitored, and shaft loads and/or jaw loads may be detected as a trigger. Tissue impedance and the like may be monitored and changes in tissue impedance (e.g., relative to clamp load) in combination with jaw gap and/or tissue position may indicate changes in tissue tension. Tissue position in jaws may be monitored and used to detect a trigger for assessing tissue tension. In the case of a tissue with no tension, under a given clamp load may have a certain area that is taken up in the jaws. If tissue tension is increased, the tissue may narrow within the jaws, which may indicate tension. Secondary devices, such as an ultrasound probe or other means, may be used to monitor tissue properties and detect a trigger for assessing tissue tension.

Semi-autonomous robotic arm repositioning may be implemented. Autonomous arm/stand repositioning may be implemented to minimize motion and/or interaction with object(s). For example, manual arm positioning in admit-tance mode may be based on geofencing (e.g., according to anatomic scans), e.g., for optimized control and reach (e.g., after a surgical instrument/device is docked on the arm; stand). Arm pre-positioning may be implemented for intro-duction of new instruments in a surgical procedure (e.g., an endocutter). existing in-use arms and/or positions (e.g., potential positions) outside a patient body may be evaluated (e.g., considered) to minimize interaction between a new arm and existing arm(s) for access to a surgical site. A virtual instrument/tool for simulation of location with end-effectors may be used (e.g., in the evaluation described herein).

Figures 12, 13A:
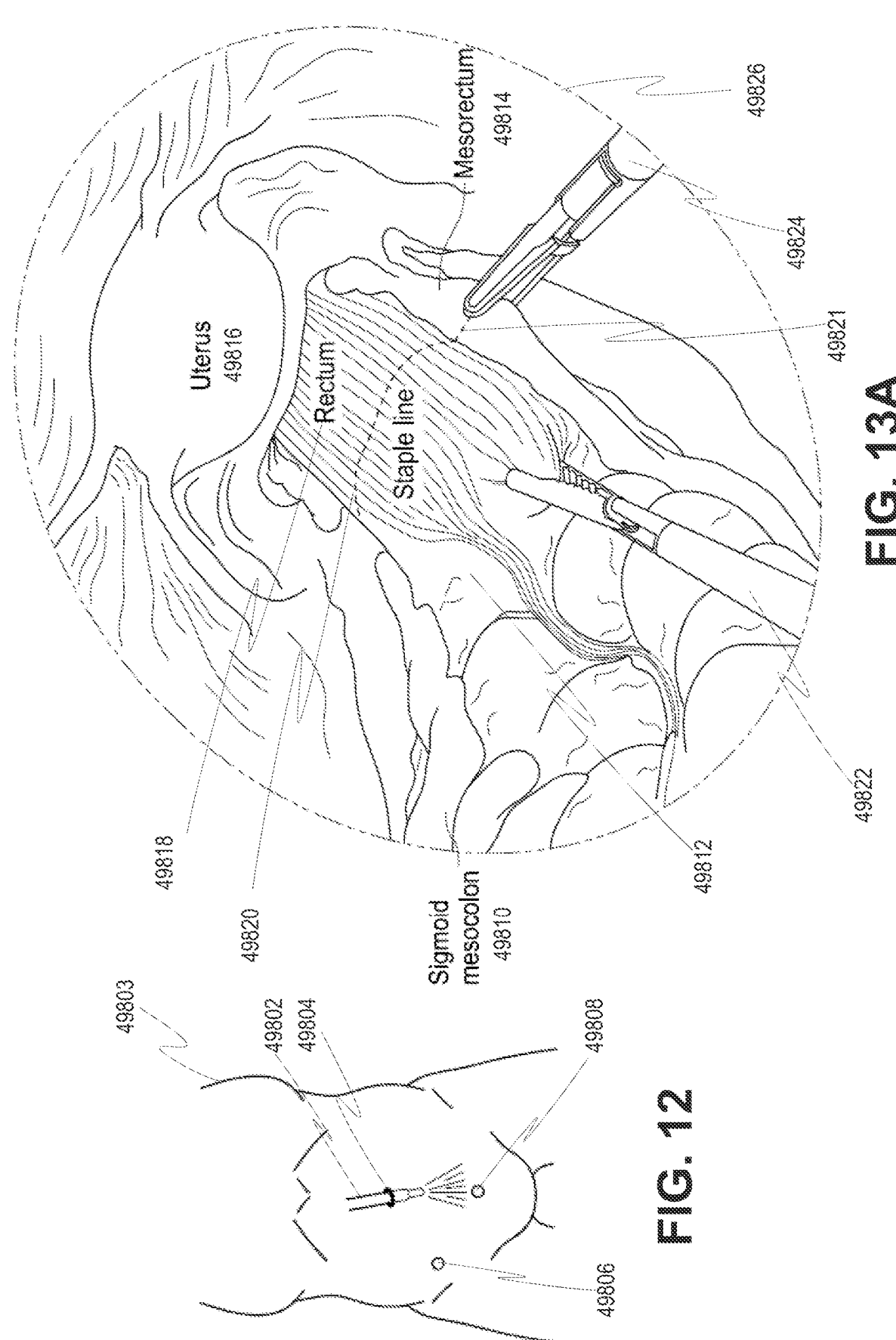
FIG. 12 illustrates example trocar placements in a laparoscopic surgical procedure.
FIG. 13A through FIG. 13C illustrate an example surgical step autonomously controlled by a computing device.

FIG. 12 illustrates example trocar placements in a lapa-roscopic surgical procedure. A first trocar port 49804 (e.g., 49718 as described in FIG. 11A through FIG. 11B) may be a port near the umbilicus (e.g., 49716 as described in FIG. 11A). A scope device (e.g., a laparoscope) 49802 may be inserted into trocar port 49804 to create a field of view (e.g., 49826 described in FIG. 13A through FIG. 13B). The field of view may be presented (e.g., via live stream) to a display device (e.g., for a healthcare professional to view). A second trocar port 49806 and a third trocar port 49808 may be two other trocar ports. Port 49806 may be a port for a grasper and port 49808 may be a port for an energy device or a linear stapler, or vice versa. The three trocar ports 49804, 49806, and 49808 form a triangulation, as described herein (e.g., in FIG. 11A through FIG. 11B).

FIG. 13A illustrates an example surgical step autono-mously controlled by a computing device. The computing device may be a robotic computing device that controls one or more surgical devices/instruments. As illustrated in FIG. 13A, field of view 49826 may be associated with a surgical procedure, such as a laparoscopic sigmoid colectomy pro-cedure. A laparoscopic sigmoid colectomy procedure may include the following surgical steps: initiate, access, mobi-lize colon, resect sigmoid, perform anastomosis, and con-clude. A surgical step may include surgical tasks. For example, the surgical step access may include the following surgical tasks: dissect adhesions, dissect mesentery, and identify ureter.

As illustrated, field of view 49826 shows the computing device performing autonomous operation associated with surgical task dissect mesentery. Field of view 49826 shows a surgical site's anatomy, which includes sigmoid mesoco-lon 49810, sigmoid colon 49812, mesorectum 49814. rec-tum 49818, and uterus 49816. Field of view 49826 shows surgical instruments for the dissect mesentery surgical task, such as a grasper 49822 and an energy device 49824.

The computing device may include a processor. The computing device (e.g., the processor included in the com-puting device) may be configured to control a surgical device to operate autonomously within a predefined bound-ary. Based on a condition being satisfied, the computing device may be configured to determine a safety adjustment to the operation. The computing device may be configured to control the surgical device to operate based on the safety adjustment.

In an example, the computing device may be configured to control grasper 49822 to operate autonomously within a predefined boundary to perform surgical task dissect mes-entery (e.g., as shown in FIG. 13A). Graspers (e.g., grasper 49822) may be used to mobilize, hold and/or place under tension a tissue (e.g., sigmoid colon 49812). The predefined boundary may be a virtual movement boundary associated with surgical task dissect mesentery.

A virtual movement boundary may be regions or adjust-able geo-fencing defined by a healthcare professional (e.g., a surgeon), e.g., to safeguard against autonomous action outside of a pre-defined area. Such pre-defined area may use healthcare professional-defined operational parameters of the autonomous operation. A surgical instrument may be allowed to operate within the operational parameters in an autonomous fashion. In an example, surgical instruments/ devices outside of the current scope field of view may be prohibited from autonomous operation. For example, a healthcare professional may draw a virtual line showing the location of the line or path to track with the surgical instrument. In such manner, the healthcare professional may set where to cut; staple and may (e.g., then) monitor the surgical instrument as the surgical instrument completes a surgical task. Variables and feedback may be processed by the computing device (e.g., in or near real time), which may enable the surgical instrument to make adjustments to the operation based on detected properties and/or behaviors. In examples, the tissue thickness may be determined during closing/closure. Wait time may be pre-programmed based on tissue type(s) and thickness in clamping jaws. Cutting speed(s) (e.g., advancing speed(s) of the cutting member, such as a knife) may be set, for example, pre-configured and/or based on the previously used parameters. In such manner, control of individual aspects of surgical instrument operation by the healthcare professional may be limited and the healthcare professional may be enabled to place addi-tional concentration on procedural step(s) (e.g., more than on each individual firing).

As illustrated in. FIG. 13A, staple line 49820 may be a virtual movement boundary defined by the healthcare professional for performing surgical step of resect sigmoid as described herein. Staple line 49820 may be marked and superimposed on the anatomy in field of view 49826 (e.g., using 3D model/augmented reality). Staple line 49820 may mark the line of resection for the surgical step of resect sigmoid. Staple line 49820 may extend to the line of dissection 49821 in mesorectum 49814 for the surgical task of dissect mesentery. In the case of energy device 49824, surgical task of dissect mesentery may be controlled to perform autonomously by a computing device, e.g., by following the dissection line 49821.

Figure 13B:
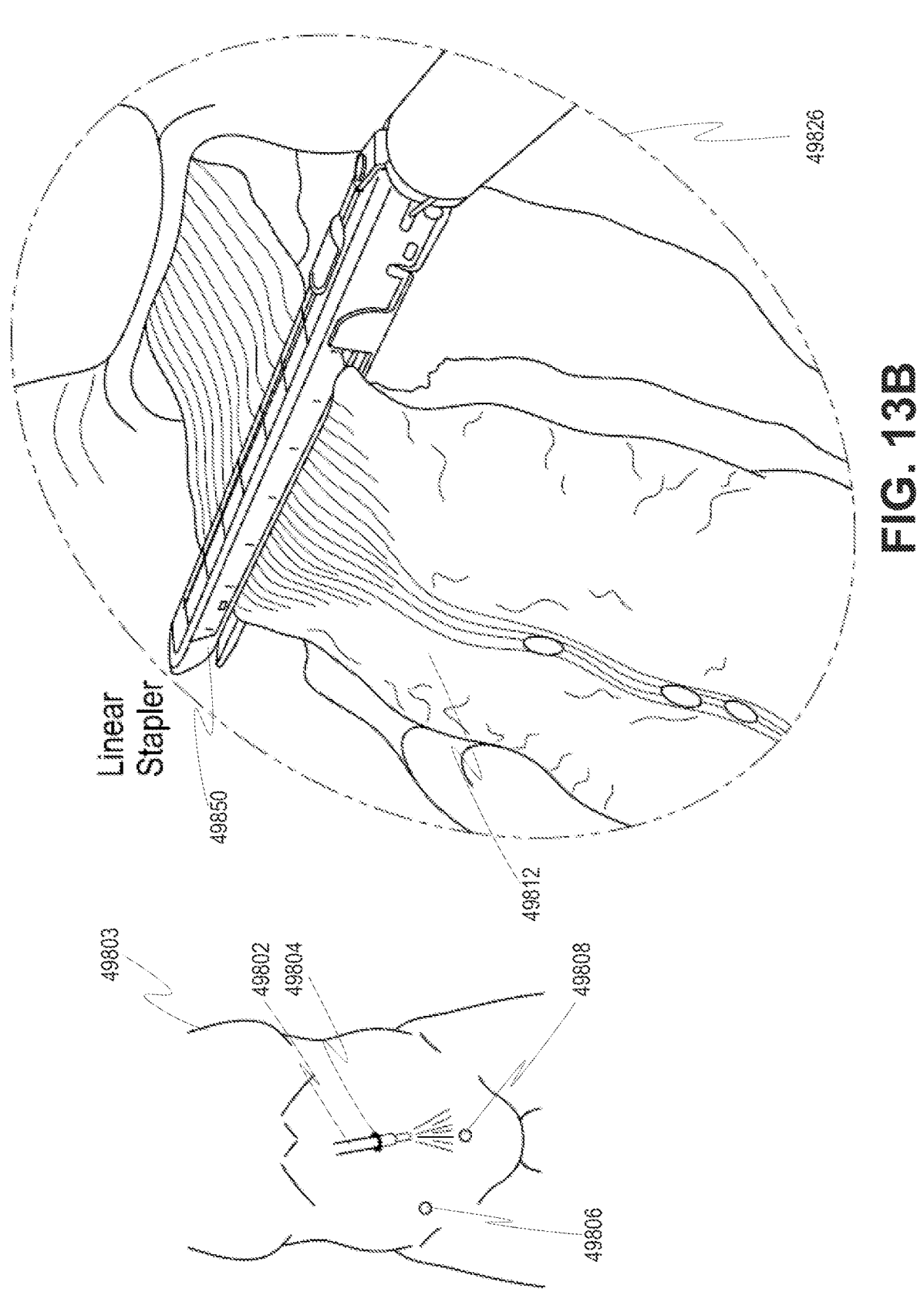

FIG. 13B illustrates an example autonomous operation of a surgical instrument. As illustrated, field of view 49826 may be associated with a laparoscopic sigmoid colectomy procedure. Field of view 49826 shows a surgical site's anatomy (e.g., as illustrated in FIG. 13A). As illustrated, operation of surgical step resect sigmoid may be autonomously controlled. As illustrated, linear stapler 49850 is controlled by the computing device to autonomously resect sigmoid colon 49812 by following staple line 49820.

Figure 13C:
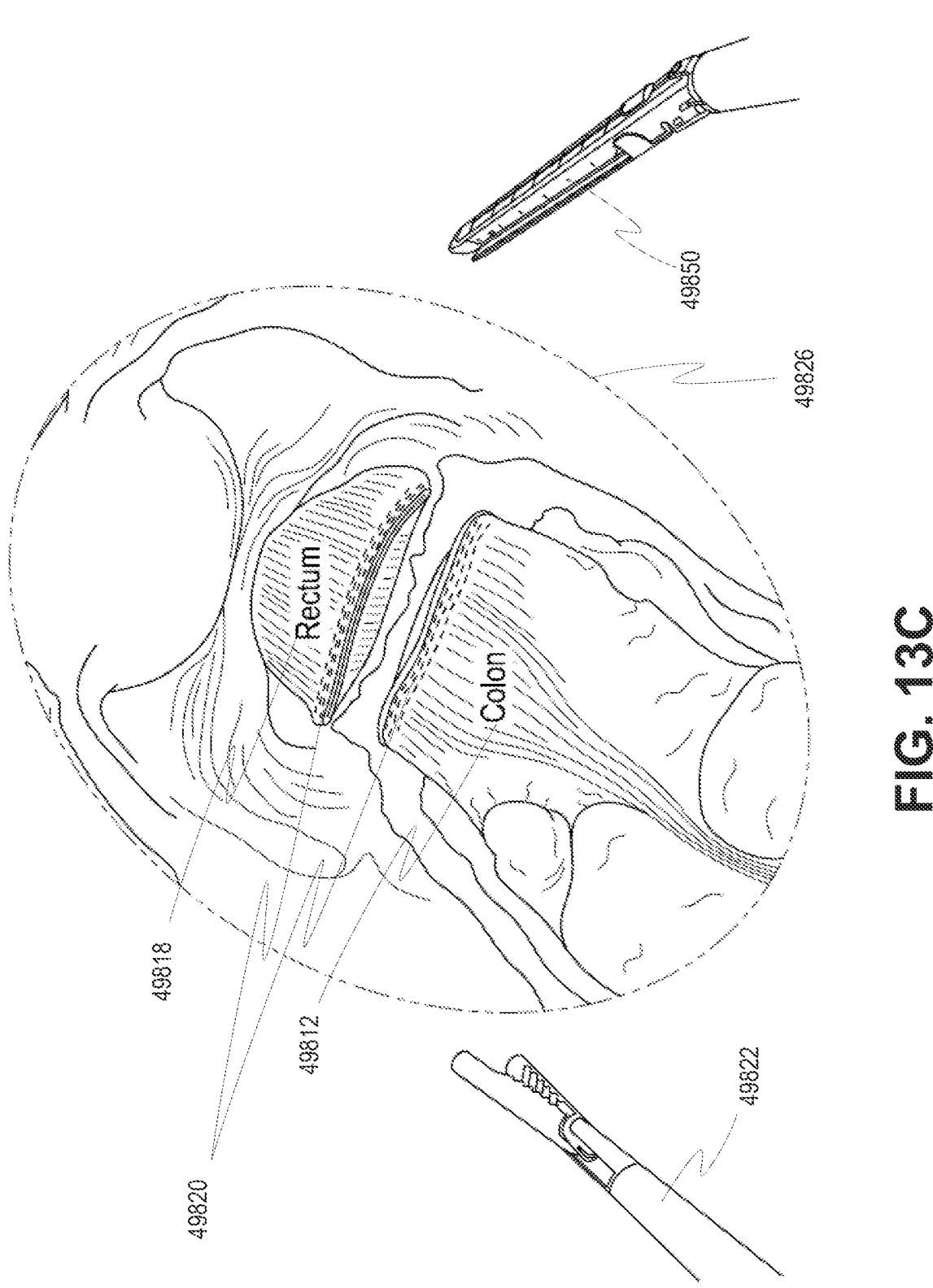

FIG. 13C illustrates an example operation of a surgical instrument. As illustrated, field of view 49826 may be associated with a laparoscopic sigmoid colectomy procedure. Field of view 49826 shows a surgical sites anatomy (e.g., as illustrated in FIG. 13A through FIG. 13B). As illustrated, autonomous operation of surgical step resect sigmoid is limited. Surgical step resect sigmoid has been completed, grasper 49822 and linear stapler 49850 are being retracted from the surgical site. In such case, autonomous operation of the jaws in grasper 49822 and/or linear stapler 49850 are locked (e.g., prohibited). Autonomous operation of the jaws in the grasper 49822 and/or the linear stapler 49850 are locked, for example, to avoid unintended damage to the tissue(s) during the retraction.

Referring to FIG. 13A, grasper 49822 may be autonomously controlled to mobilize, hold and/or place under tension a tissue (e.g., sigmoid colon 49812). The computing device may perform tissue tension measurement(s) to ensure safety related to the tissue. Strain measurements (e.g., measurement of strain applied to the tissue) may be performed. In an example, an imaging system may be used and marks (e.g., dots) may be placed on the tissue to allow relative force to be calculated on the tissue (e.g., using a 3D model of the anatomy and augmented reality). in an example, a stretchable flex circuit may be used as a temporary implantable device, for example, to provide measurements of a strain gauge and to provide information about the condition of the tissue. In an example, measurement(s) of the strain applied to grasper 49822 may be performed. The measurement(s) of the strain applied to grasper 49822 may be performed using, a strain gauge in grasper 49822. Acceleration measurements (e.g., acceleration of motion of grasper 49822) may be performed.

Sharp changes in measurements may be monitored. For example, sharp change(s) in acceleration may be detected. If acceleration starts to slow down when a constant force is applied, it may be an indication that the tissue is resistive (e.g., more resistive than average). It may be detected that there is a sudden increase in force (e.g., strain). It may be detected that there is a sudden decrease in force (e.g., strain). It may be detected that there is a transition from a steady state in force to a state where acceleration starts to increase. In such cases, it may be an indication that grasper 49822 may have lost hold of the tissue and/or grasper 49822 may have started to tear the tissue. In response, the computing device may send a control signal to grasper 49822 to cause reduction of gasping force/strain.

Measurements of strain/acceleration may be based absolute value(s). Strain/acceleration may be measured to higher than an acceptable threshold (e.g., a maximum strain/force/tension). An acceptable threshold may be based on direction of force applied to issue/grasper 49822. An acceptable threshold may be based on the force grasper 49822 may tolerate (e.g., safely). An acceptable threshold may be a speed threshold by which grasper 49822 may move, which may limit grasper's 49822 acceleration. An acceptable threshold may be movement limits that are based on the cavity of the patient being operated on. In examples, the movement limits may be (e.g., dynamically) based on the cavity size available. The movement limits may be more constrained as grasper 49822 moves closer to different parts in the body cavity.

Referring to FIG. 13B, linear stapler 49850 may be autonomously controlled to cut/staple a tissue (e.g., sigmoid colon 49812). In an example, linear stapler 49850 may be stopped of its cutting cycle before linear stapler 49850 completes the cycle and in such case linear stapler 49850 may alert that other devices/system it has stopped cutting prematurely.

In an example, in the event that a fault condition (e.g., a condition internal to the linear stapler 498501 is detected very early in the firing sequence. An inrush current for the firing sub-system of linear stapler 49850 may be monitored during the initial moments of the firing sequence. For example, 100 ms into the firing sequence, the current may be detected to be too low, and the computing device may stop linear stapler 49850 before any significant amount of firing is performed.

In an example, a fault or concern may be detected in the tissue seal quality (e.g., indicating the tissue seal is compromised), the cutting cycle may be stopped. For example, a staple may be detected to be deformed, or energy device may have faded to produce a quality seal. In such case, a subsequent cutting action may not be performed.

In an example, an instrument condition may be detected and firing type may be changed accordingly. For example, such condition may be a low battery condition or may be motor overheating condition. Under such condition(s), linear stapler 49850 may automatically change its firing mode (e.g., such as to pulsed), e.g., to be more energy/thermally efficient and to ensure the firing cycle is able to be successfully completed.

In an example, no change in firing type may be made, which may be the nominal or default state of linear stapler 49850. For example, in such case, it is assumed that everything is working correctly and there is no reason for the system to not behave in this fashion.

Linear stapler 49850 may be autonomously controlled to cut/staple a tissue (e.g., sigmoid colon 49812), e.g., based on healthcare professional selection(s). Healthcare professional selection(s) may include selection of precision or cutting cycle completion rate. In an example, a healthcare professional may select a 60 mm load for a 50 mm cut and such selection may be programmed via the computing device. In such case, the cutting cycle may stop 10 mm early and may retract at the end of the 50 mm cut. In an example, a healthcare professional may select the entire available length of the cartridge for the cutting cycle. In such case, the cutting cycle may stop al: the end of default cut cycle (e.g., a 50 mm cut with a 50 mm load).

Referring to FIG. 12, as illustrated trocar locations 49804, 49806, 49808 may be determined. Such trocar locations may be determined manually (e.g., by a human, such as a surgeon). In an example, a healthcare professional may enter a position of a trocar on a computer screen (e.g., in an OR), e.g., with assistance of laser imaging and positioning and/or an external sensor (e.g., such as a camera used for patient positioning). In such manner, absolute positioning of the trocar in space may be determined, such as position of the trocar on the patient and/or the angle at which the trocar is inserted into the patient's body.

Such trocar locations may be determined automatically (e.g., using automated Trocar insertion and final placement optimization). The computing device may suggest an optimal port placement, e.g., by causing to project laser points on a patient's body to indicate an optimal (e.g., best optimal) placement position. A healthcare professional may accept or reject such suggestion. The computing device may cause to have complete control over pressure being applied to insert the trocar. After the tip of the trocar has pierced the outer tissue, the trocar may determine that it has detected internals and in such case the knife associated with the trocar may be retracted to avoid cutting any internal structures. During the insertion, the trocar may detect obstruction and may stop the insertion. Different such trocars may be discriminated (e.g., by the computing device). Surgical instrument/device/tool may be inserted into such trocars. Such insertion may be automatic or manually performed by a healthcare professional (e.g., by a surgeon). Limits may be associated with the speed and/or forces a trocar/device may perceive. The computing device (e.g., using camera(s) and sensor(s)) may monitor the manual process and may alert the healthcare professional, if an error is detected.

Location and/or orientation of a surgical instrument/device/tool may be determined, e.g., based on associated trocar locations. In an example, when a surgical instrument/device is inserted into a trocar, the surgical instrument/device may be synchronized with the trocar automatically, In such manner, the location/orientation of the surgical instrument/device (e.g., in a body cavity) may be determined based on the location/angle of the trocar insertion. Triangulation (e.g., as shown in FIG. 11A through FIG. 11B) of the surgical instrument(s)/device(s) in the body cavity may be controlled based on the location/angle of the trocar insertion. Based on the port placement, the computing device may adjust movement of surgical instrument/device/toot to minimize movement issues. For example, the computing device may adjust movement of one surgical instrument/device/tool to reflect a trocar port placement, e.g., based on linear distance(s) and/or any distance(s).

A patient's body location/orientation may be determined. In an example, a smart hospital bed may use pressure sensors to detect where the body is and may send that information to the computing device. In an example, smart bands around key extremities (e.g., wrist(s), ankle(s), etc.) may be used to detect a patient's motion and the motion information may be used build a model of the body. Such model may guide the positioning of surgical instrument(s)/device(s) in the body cavity. In an example, a camera may capture the position of the patient and may use captured information to build a machine learning/AI model. Such model may guide the positioning of surgical instrument(s)/device(s) in the body cavity. The models described herein may help determine absolute positioning of surgical instrument(s)/device(s) in space (e.g., body cavity).

The computing device may determine movement of a surgical instrument/device and associated safety limits based on the relationship between the trocars, the patient body, and surgical instruments/devices. For example, as illustrated in FIGS. 12 and 13A, location/orientation of energy device 49824 and grasper 49822 may be determined based on location/angles of trocars 49806 and 49808, respectively, e.g., after energy device 49824 and trocar 49806 are synchronized (e.g., post-device insertion) and grasper 49822 and trocar 49808 are synchronized (e.g., post-device insertion). Patient body's 49803 location/orientation may be determined (e.g., based on a smart bed (not illustrated) the patient is lying on). In an example, the computing device may determine that a distance between energy device 49824 and grasper 49822 is below a safety threshold and may determine to cause energy device 49824 to retract by a predefined distance (e.g., 1 mm), e.g., to avoid potential collision between energy device 49824 and grasper 49822.

Confirmation, authorization, and/or initiation of intended activation of an automated step may be directed by a healthcare professional (e.g., a surgeon). The automation may be monitored, for example, via one or more authorizations of steps (e.g., a sequence of authorizations by a surgeon). In such manner, greater control over a surgical procedure may be maintained and uncertainty of the surgical procedure and/or patient-related variability may be mitigated.

A robotic system (e.g., the computing device described herein) may be trained to sequence though steps and may learn from the steps. A healthcare professional (e.g., a surgeon) may manually move surgical instruments/devices required position(s) and may acknowledge the position(s) are correct position(s) (e.g., a correction location with x, y, z coordinates). The computing device may recognize step(s) in addition to the step(s) the healthcare professional performed previously and may see authorization form the healthcare professional to add the additional step(s) to a surgical procedure map (e.g., a surgical procedure plan that includes all the steps to perform the procedure). A conditional robotic breakpoint may be used based on sensor or environmental conditions associated with the robotic system.

The computing device (e.g., a robotic system) may automatically define breakpoints based on the obvious differences in steps (e.g., that were performed by the healthcare professional) and may allow the healthcare professional to confirm the breakpoints (e.g., to provide more authorization of the breakpoints). Breakpoints may be defined based on complexity of operation, the tool, the healthcare professional training, risk, etc. In an example, the computing device may submit (e.g., place) breakpoints for further assessment (e.g., by a surgeon) before proceeding with a surgical procedure. Such obvious differences may be detected, e.g., based on monitored parameters like video stream data, tissue impendence data, force data, etc. In the case of a sleeve gastrectomy step, the staple operation may encounter mid-cycle a staple that causes it to exceed a high force threshold, which may cause a pause to allow additional creep and lower the force/trauma on the tissue. In such case, the staple operation may start back up and may automatically continue. At the end of the stroke, a clear breakpoint may occur (e.g., because a healthcare professional can clearly see the staple operation is at the end of its motion) and the staple operation may wait for the healthcare professional to allow activation of retraction after the breakpoint.

The obvious breakpoints described herein may be clear delineation(s) of a sequential set of automated steps, where a healthcare professional (e.g., a surgeon) may be verifying the operation to ensure the automation is performing the steps. In some examples, such similar operation may be part of a closed loop control.

In some examples, repeated steps may be desired, and a healthcare professional may have a means to indicate to repeal: a previous set of automated steps. A healthcare professional may be provided with the ability to modify and/or add additional steps if the healthcare professional feels the need to replicate step(s). In the case that a surgical device indicates a tissue is positioned incorrectly, the healthcare professional may request to open and reposition the surgical device. The healthcare professional may determine that more tissue needs to be removed, e.g., to ensure a good margin. The surgical device may provide the ability to adapt the sequence of steps, e.g., based on unique tissue conditions. In examples, unique tissue may be automatically recognized by the surgical device. Recognition may be based on physician knowledge or prior knowledge, such as a patient is prone to bleeding, has low blood pressure reading, etc.

During an unforeseen event, emergency, a healthcare professional may take full control of the automated steps (e.g., regardless of if it deviates from defined automated procedure steps). In an example, robotic arms may be reverted safely back to safe position(s). A system (e.g., a robotic system) may pause and may await direct command(s) from the healthcare professional.

Verification of the automation step operation or the healthcare professional initiation of the automated step may be performed by a healthcare professional (e.g., a surgeon). Verification of an out of sequence step may be performed to avoid triggering of any accidental request of the automated step. For example, the healthcare professional may partially clamp on a tissue and may accidentally initiate articulation or firing. The system may verify (e.g., with the healthcare professional) that the requested operation is intended before an automated set of steps is started. In an example, a display may not be available or part of the system. In such a case, the system may first provide hap tic feedback to the health-care professional to confirm that the healthcare professional intends to perform the detected function and subsequent reactivation may be then allowed to initiate the automation with no feedback. The healthcare professional (e.g., the surgeon) may input predefined breakpoints in the automated steps, for example, to ensure the verification and completion of an automated step.

Figure 14:
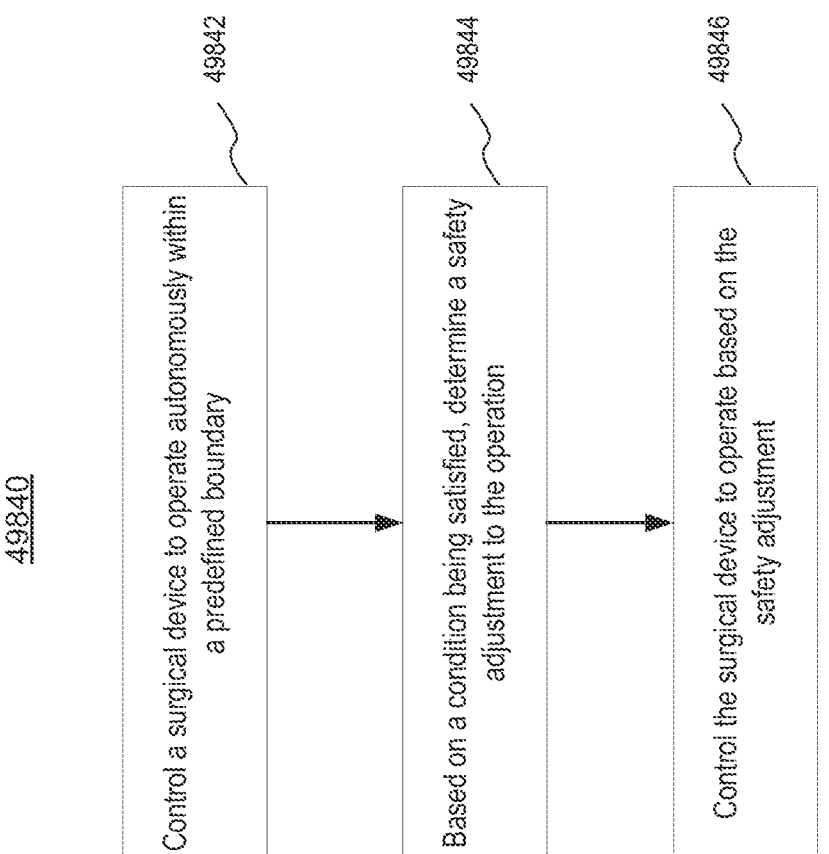
FIG. 14 is flow chart of an example autonomous operation.

FIG. 14 is a flow chart of an example autonomous operation associated with a surgical device, 49840. At 49842, a surgical device may be controlled to operate autonomously within a predefined boundary. For example, the surgical device may be a smart grasper, a smart surgical stapler, or a smart energy device. The predefined boundary may be a virtual movement boundary associated with a surgical task. The predefined boundary may be a field of view defined by a scope device.

At 49844, based on a condition being satisfied, a safety adjustment to the operation may be determined. In the case that the surgical device is a smart grasper, the condition may be a tissue tension measurement associated with the smart grasper being equal to or greater than a maximum tissue tension and the safety adjustment may be a reduction of grasping force.

In the case that the surgical device is a smart surgical stapler, the condition may be an inrush current measurement being below a lowest threshold and the safety adjustment may be stopping a firing sequence.

In the case that the surgical device is a smart energy device, first placement data associated with a first trocar and second placement data associated a second trocar may be received. The first trocar may be associated with a smart grasper and the second trocar is associated with the smart energy device. First location data associated with the smart grasper may be determined based on the first placement data. Second location data associated with the smart energy device may be determined based on the second placement data. Third location data associated with a patient body and first orientation data associated with the patient body may be received. The condition may be that a distance between the smart energy device and the smart grasper is below a threshold and the safety adjustment may be a movement adjustment of the smart energy device based on the first location data, the second location data, the third location data, and the first orientation data.

At 49846, the surgical device may be controlled to operate based on the safety adjustment. In the case that the surgical device is a smart grasper, the condition may be a tissue tension measurement associated with the smart grasper being equal to or greater than a maximum tissue tension and the safety adjustment may be a reduction of grasping force. The controlling the surgical device to operate based on the safety adjustment may comprise sending a control signal to the surgical device to cause the reduction of grasping force.

In the case that the surgical device is a smart surgical stapler, the condition may be an inrush current measurement being below a lowest threshold and the safety adjustment may be stopping a firing sequence. The controlling the surgical device to operate based on the safety adjustment may comprise stopping sending a control signal to the surgical device to cause the firing sequence to stop.

The invention claimed is:

1. A smart surgical device, the smart surgical device comprising:
a processor configured to:
   receive a first discrete signal associated with clamping control;
   generate, in response to the first discrete signal, a first continuous signal to cause a first continuous application of force based on a first autonomous control algorithm, wherein the first continuous application of the force causes the smart surgical device to control the clamping control to reach a pre-defined pressure operation range;
   obtain a first measurement that is associated with the first continuous application of the force for the clamping control, wherein the first measurement comprises a load measurement on a clamping jaw for the clamping control, a tissue measurement, and a position of a tissue;
   based on the first measurement, determine whether to autonomously adjust the first continuous application of the force;
   based on a determination to autonomously adjust the first continuous application of the force, autonomously adjust the first continuous application of the force using an updated pressure operation range;
   while the first continuous application of the force causes the smart surgical device to control the clamping control using the updated pressure operation range, autonomously generate a second continuous signal, wherein the second continuous signal is configured to cause a second continuous application of a deployment operation based on a second autonomous control algorithm, wherein the second continuous application of the deployment operation causes the smart surgical device to advance a cutting member, generate energy, and retract the cutting member;

obtain a second measurement associated with the second continuous application of the deployment operation, wherein the second measurement comprises a ratio of collagen to elastin in the tissue;

based on the second measurement, determine whether to autonomously adjust the second continuous application of the deployment operation; and based on a determination to autonomously adjust the second continuous application of the deployment operation, autonomously adjust the deployment operation based on at least the second measurement.

2. The smart surgical device of claim 1, wherein the smart surgical device is a smart surgical cutting device or a smart surgical energy device, wherein the first discrete signal is associated with initiating closure of the clamping jaw, and wherein the first discrete signal is triggered by a healthcare professional.

3. The smart surgical device of claim 1, wherein the smart surgical device is a smart surgical cutting device, wherein the first continuous application of the force is applied during at least one of: initial contact, clamping down, waiting, maintaining a pressure, or relieving the pressure.

4. The smart surgical device of claim 1, wherein the smart surgical device is a smart surgical cutting device, wherein the first measurement further comprises at least one of: a load on the clamping jaw at a first contact with the tissue, a load on the tissue when clamping down, and the tissue measurement that indicates presence of a rigid object.

5. The smart surgical device of claim 1, wherein the smart surgical device is a smart surgical cutting device.

6. The smart surgical device of claim 1, wherein the smart surgical device is a smart surgical energy device, wherein the second continuous signal is associated with initiating a firing sequence.

7. The smart surgical device of claim 1, wherein the smart surgical device is a smart surgical energy device, wherein the processor being configured to generate the energy comprises the processor being configured to generate the energy to a first pre-defined power level to at least cut the tissue or seal the tissue and wherein the processor being configured to autonomously adjust the deployment operation based on at least the second measurement comprises the processor being configured to:

adjust the energy from the first pre-defined power level to a second pre-defined power level, wherein the second pre-defined power level has a lower power level than the first pre-defined power level.

8. The smart surgical device of claim 1, wherein the smart surgical device is a smart surgical energy device, wherein the first continuous application of the force is further associated with the clamping control using the pre-defined pressure operation range and is applied during at least one of: initial contact, clamping down, waiting, or maintaining pressure.

9. The smart surgical device of claim 1, wherein the smart surgical device is a smart surgical energy device, and wherein the first measurement further comprises the position of the tissue between a clamping arm and an energy blade.

10. The smart surgical device of claim 1, wherein the smart surgical device comprises the clamping jaw controlled by the clamping control, and wherein the first continuous application of the force causes the clamping jaw to make an initial contact with the tissue, clamp down on the tissue using the pre-defined pressure operation range, maintain a pressure for the clamping jaw on the tissue, relieve pressure on the tissue, and open the clamping jaw.

11. A method, the method comprising:

receiving a first discrete signal associated with clamping control;

generating, in response to the first discrete signal, a first continuous signal to cause a first continuous application of force based on a first autonomous control algorithm, wherein the first continuous application of the force is configured to control the clamping control to reach a pre-defined pressure operation range;

obtaining a first measurement that is associated with the first continuous application of the force for the clamping control, wherein the first measurement comprises a load measurement on a clamping jaw for the clamping control, a tissue measurement, and a position of a tissue;

based on the first measurement, determining whether to autonomously adjust the first continuous application of the force;

based on a determination to autonomously adjust the first continuous application of the force, autonomously adjusting the first continuous application of the force using an updated pressure operation range;

while the first continuous application of the force is configured to control the clamping control using the updated pressure operation range, autonomously generating a second continuous signal, wherein the second continuous signal is configured to cause a second continuous application of a deployment operation based on a second autonomous control algorithm, wherein the second continuous application of the deployment operation is configured to perform advancing of a cutting member, generating of energy, and retracting the cutting member;

obtaining a second measurement associated with the second continuous application of the deployment operation, wherein the second measurement comprises a ratio of collagen to elastin in the tissue;

based on the second measurement, determining whether to autonomously adjust the second continuous application of the deployment operation; and based on a determination to autonomously adjust the second continuous application of the deployment operation, autonomously adjusting the deployment operation based on at least the second measurement.

12. The method of claim 11, wherein the method is performed by a smart surgical device, wherein the smart surgical device is a smart surgical cutting device or a smart surgical energy device, wherein the first discrete signal is associated with initiating closure of the clamping jaw, and wherein the first discrete signal is triggered by a healthcare professional.

13. The method of claim 11, wherein the method is performed by a smart surgical device, wherein the smart surgical device is a smart surgical cutting device, wherein the first continuous application of the force is applied during at least one of: initial contact, clamping down, waiting, maintaining a pressure, or relieving the pressure.

14. The method of claim 11, wherein the method is performed by a smart surgical device, wherein the smart surgical device is a smart surgical cutting device, wherein the first measurement further comprises at least one of: a load on the clamping jaw at a first contact with the tissue, a load on the tissue when clamping down, and the tissue measurement that indicates presence of a rigid object.

15. The method of claim 11, wherein the method is performed by a smart surgical device, wherein the smart surgical device is a smart surgical cutting device.

16. The method of claim 11, wherein the method is performed by a smart surgical device, wherein the smart surgical device is a smart surgical energy device, wherein the second continuous signal is associated with initiating a firing sequence.

17. The method of claim 11, wherein the method is performed by a smart surgical device, wherein the smart surgical device is a smart surgical energy device, wherein generating the energy further comprises generating the energy to a first pre-defined power level to at least cut the tissue or seal the tissue, and wherein autonomously adjusting the deployment operation based on at least the second measurement comprises:

adjusting the energy from the first pre-defined power level to a second pre-defined power level, wherein the second pre-defined power level has a lower power level than the first pre-defined power level.

18. The method of claim 11, wherein the method is performed by a smart surgical device, wherein the smart surgical device is a smart surgical energy device, wherein the first continuous application of the force is further associated with the clamping control using the pre-defined pressure operation range and is applied during at least one of: initial contact, clamping down, waiting, or maintaining pressure.

19. The method of claim 11, wherein the method is performed by a smart surgical device, wherein the smart surgical device is a smart surgical energy device, and wherein the first measurement further comprises the position of the tissue between a clamping arm and an energy blade.

20. The method of claim 11, wherein the method is performed by a smart surgical device comprising the clamping jaw controlled by the clamping control, and wherein the first continuous application of the force causes the clamping jaw to make an initial contact with the tissue, clamp down on the tissue using the pre-defined pressure operation range, maintain a pressure for the clamping jaw on the tissue, relieve pressure on the tissue, and open the clamping jaw.

* * * * *